United States Patent [19]
Altmann

[11] Patent Number: 6,051,577
[45] Date of Patent: Apr. 18, 2000

[54] N-7-HETEROCYCLYL PYRROLO[2,3-D] PYRIMIDINES AND THE USE THEREOF

[75] Inventor: Eva Altmann, Reinach, Switzerland

[73] Assignee: Novartis AG, Basel, Switzerland

[21] Appl. No.: 09/142,548

[22] PCT Filed: Mar. 5, 1997

[86] PCT No.: PCT/EP97/01095

§ 371 Date: Sep. 10, 1998

§ 102(e) Date: Sep. 10, 1998

[87] PCT Pub. No.: WO97/34895

PCT Pub. Date: Sep. 25, 1997

[30] Foreign Application Priority Data

Mar. 15, 1996 [CH] Switzerland ............... 594/96

[51] Int. Cl.[7] ............ A61K 31/519; C07D 487/04
[52] U.S. Cl. ............................ 514/258; 544/280
[58] Field of Search ............... 544/280; 514/258

[56] References Cited

FOREIGN PATENT DOCUMENTS 0 496 617  7/1992  European Pat. Off. .

*Primary Examiner*—Emily Bernhardt
*Attorney, Agent, or Firm*—Carol A. Loeschorn

[57] ABSTRACT

There are described pyrrolo[2,3]pyrimidines of formula I

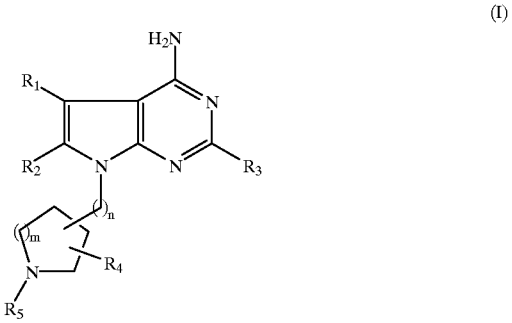

(I)

wherein $R_1$–$R_5$, m and n are as defined in the description. The compounds have valuable pharmaceutical properties and are effective especially as tyrosine protein kinase inhibitors. They can be used in the treatment of bone diseases and other diseases in warm-blooded animals that can be favorably influenced by the inhibition of tyrosine protein kinase.

7 Claims, No Drawings

N-7-HETEROCYCLYL PYRROLO[2,3-D] PYRIMIDINES AND THE USE THEREOF

The invention relates to compounds of formula I

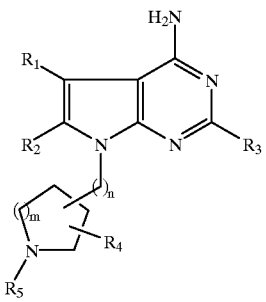

(I)

wherein
$R_1$ is aryl;
$R_2$ and $R_3$ are simultaneously or each independently of the other hydrogen, lower alkyl or halogen;
$R_4$ is hydrogen, hydroxy, unsubstituted or substituted lower alkyl, lower alkoxy, lower alkoxy-lower alkenyl, unsubstituted or substituted lower alkoxycarbonyl, N-lower alkylaminocarbonyl or N,N-di-lower alkylaminocarbonyl;
$R_5$ is hydrogen or unsubstituted or substituted lower alkyl, lower alkylcarbonyl or lower alkoxycarbonyl;
m is 1 or 2;
n is an integer from 0 to 6 inclusive;
and stereoisomers, tautomers and salts thereof, especially pharmaceutically acceptable salts; to processes for the preparation of those compounds, to pharmaceutical compositions comprising those compounds, to the use of those compounds in the therapeutic treatment of the human or animal body or in the preparation of pharmaceutical compositions.

Within the context of the present Application, the general terms used hereinbefore and hereinafter preferably have the following definitions:

The term "lower" denotes a radical having up to and including 7, and especially up to and including 6, carbon atoms.

Lower alkyl is, for example, n-propyl, isopropyl, n-butyl, isobutyl, sec-butyl, tert-butyl, n-pentyl, neopentyl, n-hexyl or n-heptyl, preferably ethyl or methyl.

Lower alkylene is, for example, methylene, ethylene or propylene, preferably methylene or ethylene.

Alkyl and alkylene are straight-chained or branched. On their own, for example as lower alkyl, or as a constituent of other groups, for example lower alkoxy, lower alkylcarbonyl, lower alkoxycarbonyl, lower alkylaminocarbonyl, di-lower alkylaminocarbonyl, lower alkoxy-lower alkenyl, they may be unsubstituted or substituted, for example by halogen, hydroxy, lower alkoxy, trifluoromethyl or morpholin-4-yl; preferably they are unsubstituted or substituted by hydroxy or amino, N-lower alkylamino or N,N-di-lower alkylamino.

Halogen is, for example, chlorine, bromine or fluorine, but may also be iodine.

Lower alkoxy is, for example, n-propoxy, isopropoxy, n-butoxy, isobutoxy, sec-butoxy, tert-butoxy, n-amyloxy or isoamyloxy, preferably methoxy or ethoxy.

Lower alkoxycarbonyl denotes the radical lower alkyl—O—C(O)— and is, for example, n-propoxycarbonyl, isopropoxycarbonyl, n-butoxycarbonyl, isobutoxycarbonyl, sec butoxycarbonyl, tert-butoxycarbonyl, n-amyloxycarbonyl or isoamyloxycarbonyl, preferably methoxycarbonyl or ethoxycarbonyl.

Lower alkylamino is, for example, n-propylamino, n-butylamino, isopropylamino or isobutyl-amino, preferably methylamino or ethylamino.

Di-lower alkylamino is, for example, dimethylamino, diethylamino, di-n-propylamino, n-butyl-amino, di-n-butylamino or n-propyl-n-butylamino, preferably dimethylamino, diethylamino or methylethylamino.

N-Lower alkylaminocarbonyl is, for example, N-methylcarbamoyl, N-ethylcarbamoyl, N-n-propylcarbamoyl or N-isopropylcarbamoyl, preferably N-methylcarbamoyl or N-ethyl-carbamoyl.

N,N-Di-lower alklaminocarbonyl is, for example, N,N-dimethylcarbamoyl, N,N-diethyl-carbamoyl, N-methyl-N-ethylcarbamoyl, N,N-di-n-propylcarbamoyl or N-methyl-N-isopropyl-carbamoyl, preferably N,N-dimethylcarbamoyl, N,N-diethylcarbamoyl or N-methyl-N-ethylcarbamoyl.

Aryl is, for example, phenyl or naphthyl, each of which is unsubstituted or substituted, for example as indicated hereinafter for phenyl. Aryl is preferably phenyl unsubstituted or substituted by one or more, for example from one to three, especially one or two, substituents from the group consisting of lower alkyl, halo-lower alkyl, (hydroxy or lower alkanoyloxy)-lower alkyl, lower alkoxy-lower alkyl, (hydroxy, lower alkoxy or lower alkanoyl-oxy)-lower alkoxy-lower alkyl, (amino, lower alkylamino, di-lower alkylamino or lower alkanoylamino)-lower alkoxy-lower alkyl, (amino or lower alkanoylamino)-lower alkyl, lower alkylamino-lower alkyl, di-lower alkylamino-lower alkyl; azacycloalkyl-lower alkyl, for example (piperidinyl, piperazinyl, morpholinyl or pyrrolidinyl)-lower alkyl; azaheteroaryl-lower alkyl, for example (imidazolyl, triazolyl, pyridyl, pyrimidinyl or pyrrolyl)-lower alkyl, (hydroxy, lower alkoxy or lower alkanoyloxy)-lower alkylamino-lower alkyl, (amino, lower alkylamino, di-lower alkylamino or lower alkanoylamino)-lower alkylamino-lower alkyl; azacycloalkyl-lower alkylamino-lower alkyl, for example (piperidinyl, piperazinyl, morpholinyl or pyrrolidinyl)-lower alkylamino-lower alkyl; azaheteroaryl-lower alkylamino-lower alkyl, for example (imidazolyl, triazolyl, pyridyl, pyrimidinyl or pyrrolyl)-lower alkylamino-lower alkyl; mercapto-lower alkyl, lower alkyl-(thio, sulfinyl or sulfonyl)-lower alkyl, (hydroxy, lower alkoxy or lower alkanoyloxy)-lower alkyl-(thio, sulfinyl or sulfonyl)-lower alkyl, (amino, lower alkylamino, di-lower alkylamino or lower alkanoylamino)-lower alkyl-(thio, sulfinyl or sulfonyl)-lower alkyl, carboxy-lower alkyl, lower alkoxycarbonyl-lower alkyl, aminocarbonyl-lower alkyl, N-lower alkylaminocarbonyl-lower alkyl, N,N-di-lower alkylaminocarbonyl-lower alkyl, hydroxy, lower alkoxy, lower alkanoyloxy, $C_1$–$C_3$alkylenedioxy, phenyl-lower alkoxy, (hydroxy, lower alkoxy or lower alkanoyloxy)-lower alkoxy, (amino or lower alkanoylamino)-lower alkoxy, lower alkylamino-lower alkoxy, di-lower alkylamino-lower alkoxy, azacycloalkyl-lower alkoxy, for example (piperidinyl, piperazinyl, morpholinyl or pyrrolidinyl)-lower alkoxy; azaheteroaryl-lower alkoxy, for example (imidazolyl, triazolyl, pyridyl, pyrimidinyl or pyrrolyl)-lower alkoxy; (hydroxy, lower alkoxy or lower alkanoyloxy)-lower alkylamino-lower alkoxy, (amino, lower alkylamino, di-lower alkylamino or lower alkanoylamino)-lower alkylamino-lower alkoxy; azacycloalkyl-lower alkylamino-lower alkoxy, for example (piperidinyl, piperazinyl, morpholinyl or pyrrolidinyl)- lower alkylamino-lower alkoxy; azaheteroaryl-lower alkylamino-lower alkoxy, for example (imidazolyl, triazolyl, pyridyl, pyrimidinyl or pyrrolyl)-lower alkylamino-lower alkoxy; (hydroxy, lower alkoxy or lower alkanoyloxy)-lower alkoxy-lower alkoxy, (amino, lower alkylamino, di-lower alkylamino or lower alkanoylamino)-lower alkoxy-lower alkoxy, (hydroxy, lower alkoxy or lower alkanoyloxy)-lower alkyl-(thio, sulfinyl or sulfonyl)-lower alkoxy, (amino, lower alkylamino, di-lower alkylamino or lower alkanoyl-amino)-lower alkyl-(thio, sulfinyl or sulfonyl)-lower alkoxy, hydroxysulfonyl-lower alkoxy, carboxy-lower alkoxy, lower alkoxycarbonyl-lower alkoxy, aminocarbonyl-lower alkoxy, N-lower alkylaminocarbonyl-lower alkoxy, N,N-di-lower alkylaminocarbonyl-lower alkoxy, amino, lower alkylamino, di-lower alkylamino, lower alkanoylamino; azacycloalkyl, for example piperidinyl, piperazinyl, morpholinyl or pyrrolidinyl; azaheteroaryl, for example imidazolyl, triazolyl, pyridyl, pyrimidinyl or pyrrolyl; mercapto, lower alkyl-(thio, sulfinyl or sulfonyl), (hydroxy, lower alkoxy or lower alkanoyloxy)-lower alkyl-(thio, sulfinyl or sulfonyl), (amino, lower alkylamino, di-lower alkylamino or lower alkanoylamino)-lower alkyl-(thio, sulfinyl or sulfonyl), (hydroxy, lower alkoxy or lower alkanoyloxy)-lower alkoxy-lower alkyl-(thio, sulfinyl or sulfonyl), (amino, lower alkylamino, di-lower alkylamino or lower alkanoyl-amino)-lower alkoxy-lower alkyl-(thio, sulfinyl or sulfonyl), (hydroxy, lower alkoxy or lower alkanoyloxy)-lower alkylamino-lower alkyl-(thio, sulfinyl or sulfonyl), (amino, lower alkyl-amino, di-lower alkylamino or lower alkanoylamino)-tower alkylamino-lower alkyl-(thio, sulfinyl or sulfonyl), carboxy-lower alkylthio, lower alkoxycarbonyl-lower alkylthio, amino-carbonyl-lower alkylthio, N-lower alkylaminocarbonyl-lower alkylthio, N,N-di-lower alkyl-aminocarbonyl-lower alkylthio, halogen, carboxy, lower alkoxycarbonyl, aminocarbonyl, N-lower alkylaminocarbonyl, N-[(hydroxy, lower alkoxy or lower alkanoyloxy)-lower alkyl]-aminocarbonyl, N-[(amino, lower alkylamino, di-lower alkylamino or lower alkanoylamino)-lower alkyl]-aminocarbonyl; [azacycloalkyl-lower alkyl]-aminocarbonyl, for example N-[(piperidinyl, piperazinyl, morpholinyl or pyrrolidinyl)-lower alkyl]-aminocarbonyl; [aza-heteroaryl-lower alkyl-aminocarbonyl, for example N-[(imidazolyl, triazolyl, pyridyl, pyrimidinyl or pyrrolyl)-lower alkyl]-aminocarbonyl; N-(hydroxysulfonyl-lower alkyl)-aminocarbonyl, N,N-di-lower alkylaminocarbonyl, cyano, amidino, formamidino and guanidino and, for example, nitro, lower alkanoyl and benzoyl.

In substituents containing groups such as, for example, hydroxy-lower alkoxy, amino-lower alkoxy, hydroxy-tower alkylamino, amino-lower alkylamino, hydroxy-lower alkylthio or amino-lower alkylthio, the two hetero atoms are preferably separated from one another by at least two carbon atoms; in other words, the lower alkyl moiety is preferably so selected that there are at least two carbon atoms between the two hetero atoms.

Azacycloalkyl is a cycloalkyl radical having from 3 to 8, especially from 5 to 7, ring atoms, at least one of the ring atoms being a nitrogen atom. Azacycloalkyl may also contain further ring hetero atoms, for example N, O or S; it is, for example, piperidinyl, piperazinyl, morpholinyl or pyrrolidinyl.

Azaheteroaryl is an aromatic radical having from 3 to 7, especially from 5 to 7, ring atoms, at least one of the ring atoms being a nitrogen atom. Azaheteroaryl may also contain further ring hetero atoms, for example N, O or S. It may also be partially saturated. Azaheteroaryl is, for example, imidazolyl, triazolyl, pyridyl, pyrimidinyl or pyrrolyl.

Radicals such as piperidinyl, piperazinyl, morpholinyl, pyrrolidinyl, imidazolyl, triazolyl and pyrrolyl can be bonded via a ring nitrogen atom or a ring carbon atom, and radicals such as pyridyl or pyrimidinyl are preferably bonded via a carbon atom.

The azacycloalkyl radicals bonded via a ring nitrogen atom, which are preferred, are referred to in known manner as piperidino, piperazino, morpholino, pyrrolidino, etc.

The compounds I and their salts may be in the form of one of the possible isomers, for example stereoisomers, diastereoisomers or tautomers, or in the form of a mixture thereof. There are obtainable as pure isomers, for example, pure enantiomers, pure diastereoisomers or, where appropriate, pure tautomers. Accordingly, mixtures of isomers may be in the form of, for example, racemates or mixtures of diastereoisomers.

Salts of compounds of formula I are especially pharmaceutically acceptable salts, especially acid addition salts with suitable mineral acids, such as hydrohalic acids, sulfuric acid or phosphoric acid, for example hydrochlorides, hydrobromides, sulfates, hydrogen sulfates or phosphates, salts with suitable aliphatic or aromatic sulfonic acids or N-substituted sulfamic acids, for example methanesulfonates, benzenesulfonates, p-toluenesulfonates or N-cyclo-hexylsulfamates (cyclamates), or salts with strong organic carboxylic acids, such as lower alkanecarboxylic acids or saturated or unsaturated or hydroxylated aliphatic dicarboxylic acids, for example acetates, oxalates, malonates, maleates, fumarates, tartrates or citrates.

Also possible, where the compounds of formula I contain an acid group, are corresponding salts with bases, for example corresponding alkali metal or alkaline earth metal salts, for example sodium, potassium or magnesium salts, pharmaceutically acceptable transition metal salts, such as zinc or copper salts, or salts with ammonia or organic amines, such as cyclic amines, mono-, di- or tri-lower alkylamines, hydroxy-lower alkylamines, for example mono-, di- or tri-hydroxy-lower alkylamines, hydroxy-lower alkyl-lower alkyl-amines or poly-hydroxy-lower alkylamines. Cyclic amines are, for example, morpholine, thiomorpholine, piperidine or pyrrolidine. Suitable mono-lower alkylamines are, for example, ethyl- and tert-butyl-amine; suitable di-lower alkylamines are, for example, diethyl- and diisopropyl-amine and suitable tri-lower alkylamines are, for example, trimethyl- and triethyl-amine. Suitable hydroxy-lower alkylamines are, for example, mono-, di- and tri-ethanolamine; suitable hydroxy-lower alkyl-lower alkyl-amines are, for example, N,N-dimethylamino- and N,N-diethylamino-ethanol. Compounds of formula I having an acid group, for example carboxy, and a basic group, for example amino, may also be in the form of, for example, internal salts, i.e. in zwitterionic form, or part of the molecule may be in the form of an internal salt and another part in the form of a normal salt. Pharmaceutically unacceptable salts are also included, since they can be used, for example, for the isolation and/or purification of free compounds I and the pharmaceutically acceptable salts thereof.

The compounds of formula I have valuable pharmacological properties. In particular, they inhibit the activity of tyrosine protein kinase pp60$^{c-src}$ in concentrations of from approximately 0.001 to approximately 10 $\mu$M [test description: K. Farley et al., *Anal. Biochem.* 203 (1992) 151–157; purified enzyme—as described in N. B. Lydon et al., *Biochem. J.* 287 (1992) 985–993—is used].

It is known that both targeted modification of the c-src gene leading to the elimination of c-src and inhibition of the activity of tyrosine protein kinase pp60$^{c-src}$ affect the bone absorption ability of osteoclasts [for elimination of c-src by gene manipulation see, for example, P. Soriano et al., *Cell* 64 (1991) 693–702; for inhibition of the activity of tyrosine protein kinase pp60$^{c-src}$ see, for example, B. F. Boyce et al., *J. Clin. Invest.* 90 (1992) 1622–1627; T. Yoneda et al., *J. Clin. Invest.* 91 (1993) 2791–2795].

Owing to their inhibitory activity against tyrosine protein kinase pp60$^{c-src}$, the compounds of formula I are therefore capable of inhibiting the bone absorption ability of osteoclasts. That can be demonstrated, for example, in the bone slice assay on bovine cortical bone platelets with rat osteoclasts in concentrations of from approx. 0.001 to approx 10 μM. (The "bone slice assay" is described, for example, in *Biochem. Biophys. Res. Comm.* 188 (1992) 1097–1103]. In that assay, the compounds of formula I inhibit the formation of characteristic absorption holes in bone platelets in vitro.

In vivo, the effectiveness of compounds of formula I can be demonstrated, for example, in the Hock model in the rat. In that test, the compounds of formula I—when administered once a day per os in concentrations of from approx. 1 to approx 100 mg/kg of body weight—for from 3 to 4 weeks completely or at least partially inhibit the bone loss produced as a result of ovariectomy in rats [the "Hock model" is described, for example, in *Metab. Bone Dis.* 5 (1984) 177–181].

The in vivo effectiveness of compounds of formula I can also be demonstrated, for example, via calcium metabolism in intact rats. In that method, after i.v. injection of the test compound acute hypocalcaemia is induced within from 1 to 4 hours, this being demonstrated by determining the concentration of calcium in the blood plasma. The observation of acute hypocalcaemia can be interpreted as indirect evidence that the test compound inhibits bone absorption.

The compounds of formula I are therefore very suitable for the treatment of diseases that are responsive to inhibition of the activity of tyrosine protein kinase pp60$^{c-src}$. Special mention may be made here of osteoporosis, and of other diseases in the course of which the absorption of bone by osteoclasts plays a role, such as tumour-induced hypercalcaemia or Paget's disease, or the treatment of bone metastases, and also inflammatory processes in joints and bones and degenerative processes in cartilage tissue. In addition, the compounds of formula I are useful in the treatment of benign or malignant tumours that respond to inhibition of tyrosine protein kinase pp60$^{c-src}$, such as breast cancer (mammary carcinoma) or intestinal cancer (colon carcinoma). They are capable of effecting tumour regression and of preventing the formation of tumour metastases and the growth of micrometastases. The compounds of formula I are also useful in the treatment of cardiovascular diseases, such as thrombosis.

The compounds of formula I also inhibit the activity of other non-receptor tyrosine protein kinases, such as (a) other members of the src family, for example lck and fyn, (b) abl kinase and (c) ZAP70 kinase. Furthermore, the compounds of formula I also inhibit the activity of receptor tyrosine protein kinases, such as (a) the EGF family, for example the EGF receptor, c-erbB2, c-erbB3 and c-erbB4, and (b) the PDGF family, for example the PDGF receptor, CSF-1, Kit, VEGF and FGF. Owing to those actions, the compounds of formula I can also be used in immunomodulation and in the treatment of diseases of the immune system, for example in the case of inflammations or organ transplants. They are also suitable for the treatment of (hyper)proliferative diseases, such as psoriasis, tumours, carcinomas and leukaemias, and in fibrosis and restenosis. The compounds of formula I can also be used in the treatment of diseases of the central or the peripheral nervous system where signal transmission by at least one tyrosine protein kinase is involved.

Preferably the invention relates to compounds of formula I wherein $R_1$ is phenyl unsubstituted or substituted by one, two or three substituents from the group consisting of lower alkyl, hydroxy-lower alkyl, phenyl, lower alkoxy, phenyl-lower alkoxy, $C_1$–$C_3$alkylenedioxy, cyano and halogen;

$R_2$ and $R_3$ are simultaneously or each independently of the other hydrogen, lower alkyl or halogen;

$R_4$ is hydrogen, hydroxy, unsubstituted or substituted lower alkyl, lower alkoxy, lower alkyleneoxy-lower alkyl, unsubstituted or substituted lower alkoxycarbonyl, N-lower alkylaminocarbonyl or N,N-di-lower alkylaminocarbonyl;

$R_5$ is hydrogen or unsubstituted or substituted lower alkyl, lower alkylcarbonyl or lower alkoxycarbonyl;

m is 1 or 2;

n is an integer from 0 to 4 inclusive;

and salts thereof.

The invention relates especially to compounds of formula I wherein $R_1$ is phenyl unsubstituted or substituted by one, two or three substituents from the group consisting of lower alkyl, hydroxy-lower alkyl, phenyl, lower alkoxy, phenyl-lower alkoxy, $C_1$–$C_3$alkylenedioxy, cyano and halogen;

$R_2$ and $R_3$ are hydrogen;

$R_4$ is hydrogen, hydroxy, unsubstituted or substituted lower alkyl, lower alkoxy, lower alkyleneoxy-lower alkyl, unsubstituted or substituted lower alkoxycarbonyl, N-lower alkyl-aminocarbonyl or N,N-di-lower alkylaminocarbonyl;

$R_5$ is hydrogen or unsubstituted or substituted lower alkyl, lower alkylcarbonyl or lower alkoxycarbonyl;

m is 1 or 2;

n is an integer from 0 to 4 inclusive;

and salts thereof.

The invention relates more especially to compounds of formula I wherein $R_1$ is phenyl unsubstituted or substituted by one, two or three substituents from the group consisting of lower alkyl, hydroxy-lower alkyl, phenyl, lower alkoxy, phenyl-lower alkoxy, $C_1$–$C_3$alkylenedioxy, cyano and halogen;

$R_2$ and $R_3$ are hydrogen;

$R_4$ is hydrogen, unsubstituted or substituted lower alkyl, lower alkoxy, lower alkyleneoxy-lower alkyl or unsubstituted or substituted lower alkoxycarbonyl;

$R_5$ is hydrogen or unsubstituted or substituted lower alkyl, lower alkylcarbonyl or lower alkoxycarbonyl;

m is 1 or 2;

n is 0 or 1;

and salts thereof.

The invention relates very especially to compounds of formula I wherein $R_1$ is phenyl unsubstituted or substituted by one, two or three substituents from the group consisting of lower alkyl, hydroxy-lower alkyl, phenyl, lower alkoxy, phenyl-lower alkoxy, $C_1$–$C_3$alkylenedioxy, cyano and halogen;

$R_2$ and $R_3$ are hydrogen;

$R_4$ is hydrogen, unsubstituted or substituted lower alkyl, lower alkoxy, lower alkyleneoxy-lower alkyl or unsubstituted or substituted lower alkoxycarbonyl;

$R_5$ is hydrogen or unsubstituted or substituted lower alkyl, lower alkylcarbonyl or lower alkoxycarbonyl;

m is 1 or 2;
n is 0;
and pharmaceutically acceptable salts thereof.

The invention relates especially to the specific compounds described in the Examples and salts thereof.

The compounds of formula I can be prepared in a manner known per se, for example, by (a) subjecting a compound of formula II

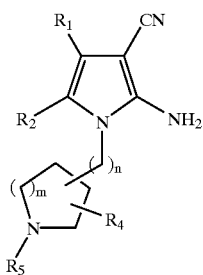
(II)

to a ring closure reaction with synthesis of the pyrimidine ring, or (b) subjecting a compound of formula III

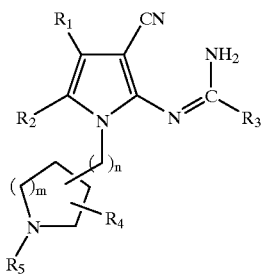
(III)

to a ring closure reaction with synthesis of the pyrimidine ring, or (c) reacting a compound of formula IV

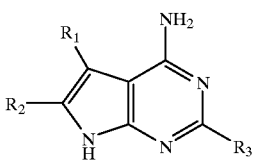
(IV)

with a compound of formula V

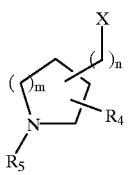
(V)

wherein X is a leaving group; or (d) reacting a compound of formula VI

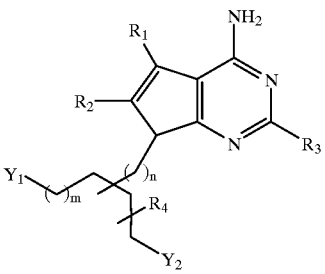
(VI)

wherein $Y_1$ and $Y_2$ are suitable leaving groups, for example halogen, especially chlorine, with a compound of formula VII $$R_5—NH_2 \quad (VII)$$

and, if desired, converting a compound of formula I into a different compound of formula I, and/or, if desired, converting a resulting salt into the free compound or into a different salt, and/or, if desired, converting a resulting free compound of formula I having salt-forming properties into a salt.

In the more detailed description of the processes that follows, unless otherwise indicated each of the symbols $R_1$ to $R_5$ is as defined for formula I.

Process (a): The reaction according to process (a) corresponds to the cyclisation known per se of 2-amino-3-cyano-pyrroles to 4-amino-pyrrolo[2,3-d]pyrimidines (see, for example, H. Pichler et al., *Liebigs Ann. Chem.* 1986, 1485–1505). Suitable cyclisation reagents are, for example, (1) formamide or (2) 1. trialkyl orthoformate/2. ammonia. The cyclisation of compounds of formula it with formamide is preferably carried out at elevated temperature, for example at 160° C., and advantageously with the addition of a small amount of dimethyl-formamide and formic acid. The reaction of compounds of formula II with trialkyl orthoformate to give the corresponding alkoxy formimidates formed as intermediates normally takes place at less elevated temperatures, for example at from 80 to 120° C. The cyclisation of the latter with ammonia is then generally carried out again at relatively high temperatures, for example at 130° C. in an autoclave.

The compounds of formula II are preferably prepared using one of the known methods of pyrrole synthesis. They are obtained, for example, by reacting a compound of formula IIa

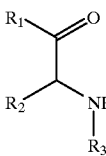
(IIa)

with malonic acid dinitrile, preferably in the presence of a base, for example sodium ethanolate/ethanol.

The compounds of formula IIa can themselves be prepared, for example, by reacting a compound $R_1$—C(=O)—CH(-$R_2$)—Hal[Hal=halogen], that is to say, for example, phenacyl bromide or chloride, with a compound $H_2N$—$R_3$, for example aniline, preferably in the presence of a base, for example sodium carbonate/ethanol or triethylamine/toluene.

Process (b): The ring closure to form the corresponding 4-amino-pyrrolo[2,3-d]pyrimidine is carried out, for example, in the presence of suitable bases, for example sodium ethanolate/ethanol, preferably at elevated temperature, for example at 80° C. [see, for example, E. C. Taylor et al., *J. Amer. Chem. Soc.* 87 (1965) 1995–2003].

The amidine compounds of formula III can be prepared, for example, from the corresponding amino compounds of formula II in accordance with known methods of amidine synthesis, for example by reaction first with triethyl orthoformate, preferably at elevated temperature, and then with ammonia, preferably at room temperature.

Process (c): Suitable leaving groups are, for example, methanesulfonates or p-toluenesulfonates of hydroxy compounds and halogen. The preparation of suitable pyrrolo[2,3-d]pyrimidines of formula IV is known from the literature or can be carded out analogously to processes described in the literature. The reaction of compounds of formula IV with compounds of formula V is carried out in a manner known per se. For example, a methane-sulfonate of formula V is reacted with a pyrrolo[2,3-d]pyrimidine of formula IV in the presence of a base, for example potassium carbonate. The reaction is preferably carried out at elevated temperature, for example at from 50° C. to the reflux temperature of the reaction mixture, especially at from 60 to 80° C., and advantageously in an inert solvent or solvent mixture. The reaction can be accelerated in an advantageous manner by the addition of a suitable crown ether. In a further process, the reaction takes place in a manner known per se under the conditions of phase transfer catalysis (E. V. Dehmlow and S. S. Dehmlow, *Phase Transfer Catalysis*, 3rd ed., VCH, Weinheim, 1993). The reactants of formulae IV and V are dissolved in a suitable inert solvent or solvent mixture, and the second phase is formed by a concentrated aqueous alkali metal hydroxide solution, for example 30% sodium hydroxide solution. Advantageously, a phase transfer catalyst, for example a quaternary ammonium halide, such as tetrabutylammonium bromide, is added.

Process (d): The reaction of a compound of formula VI with an amine is carried out in a manner known per se. It is carried out advantageously in an inert solvent or solvent mixture with cooling, at ambient temperature or at elevated temperature up to the reflux temperature of the reaction mixture, especially with ice-cooling, at room temperature or at elevated temperature up to the reflux temperature. The reaction may also be carried out with or without solvent in a bomb tube. Compounds of formula VI are obtained, for example, by reacting an optionally protected compound of formula IV with a compound of formula VIa

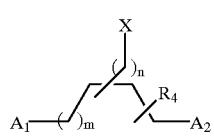

(VIa)

wherein X is a suitable leaving group, for example a methanesulfonate or p-toluene-sulfonate, and $A_1$ and $A_2$ are radicals that are stable under the reaction conditions and can subsequently be converted readily into leaving groups $Y_1$ and $Y_2$. For example, $A_1$ and $A_2$ may be silyl ether radicals, especially tert-butyldimethylsilyl ether radicals, which can be cleaved in a manner known per se after the reaction of an optionally protected compound IV with a compound VIa, resulting in an optionally protected compound of the general formula VI wherein $Y_1$ and $Y_2$ are hydroxyl radicals. Those hydroxyl radicals can then be converted in a manner known per se into other leaving groups, for example halogen. The reaction of an optionally protected compound of formula IV with a compound of formula VIa can be carried out, for example, analogously to the reaction, described for process c), of a compound of formula IV with a compound of formula V.

Compounds of formula I can be converted into other compounds of formula I.

For example, in a manner known per se substituents in the aryl radical $R_1$ can be converted into one another.

For example, halo-lower alkyl, e.g. chloromethyl, can be reacted, for example, with unsubstituted or substituted lower alkanols, lower alkanethiols or lower alkylamines in accordance with a nucleophilic substitution reaction, yielding unsubstituted or substituted lower alkoxy-lower alkyl lower alkylthio-lower alkyl or lower alkylamino-lower alkyl, respectively.

Hydroxy can be reacted, for example, with unsubstituted or substituted halo-lower alkanes, yielding unsubstituted or substituted lower alkoxy. Hydroxy can, for example, also be reacted initially with a di-halo-lower alkane, for example 1-bromo-2-chloroethane, yielding $\Omega$-halo-lower alkoxy; the latter can be reacted in a manner analogous to that described above with unsubstituted or substititued lower alkanols, lower alkanethiols or lower alkylamines in accordance with a nucleophilic substitution reaction, yielding unsubstituted or substituted lower alkoxy-lower alkoxy, lower alkylthio-lower alkoxy or lower alkylamino-lower alkoxy, respectively.

Analogously to hydroxy, mercapto can also be alkylated as described in the preceding paragraph.

Lower alkylthio groups can be converted by controlled oxidation both into lower alkylsulfinyl groups and into lower alkylsulfonyl groups.

Amino groups and hydroxy groups can be acylated in known manner, yielding, for example, lower alkanoylamino or lower alkanoyloxy groups, respectively.

Carboxylic acid radicals can be converted in accordance with known derivatisation methods, such as esterification or amide formation, into carboxylic acid derivatives, such as lower alkoxycarbonyl, aminocarbonyl, N-lower alkylaminocarbonyl, N,N-di-lower alkylaminocarbonyl, cyano or amidino. Conversely, carboxylic acid derivatives can also be converted into free carboxylic acids, for example by hydrolysis.

Compounds of formula I wherein $R_2$ is hydrogen can be converted by reaction with a halogenating agent, for example a N-halosuccinimide, into compounds of formula I wherein $R_2$ is halogen.

Substituents in the radicals $R_4$ and $R_5$ can be converted in a manner known per se into other substituents.

For example, hydroxy groups can be esterified with organic or inorganic acids or etherified with alcohols or organic halides or they can be removed by reduction If any of the intermediates contain troublesome reactive groups, for example carboxy, hydroxy, mercapto or amino groups, those groups can be protected temporarily by readily removable protecting groups. The choice of suitable protecting groups, their introduction and their removal are known per se and are described, for example, in J. F. W. McOmie, *Protective Groups in Organic Chemistry*, Plenum Press, London, New York 1973, and also, for example, in T. W. Greene and P. G. M. Wuts, *Protective Groups in Organic Synthesis*, Wiley, New York et al. 1991, or in P. J. Koclensld, *Protecting Groups*, Thieme, Stuttgar, New York 1994.

Salts of compounds I can be prepared in a manner known per se. For example, acid addition salts of compounds I are obtained by treatment with a suitable acid or a suitable ion exchange reagent and salts with bases are obtained by treatment with a suitable base or a suitable ion exchange reagent. Salts of compounds of formula I can be converted into the free compounds I in customary manner; acid addition salts, for example, by treatment with a suitable basic agent or a suitable ion exchange reagent and salts with bases, for example, by treatment with a suitable acid or a suitable ion exchange reagent.

Salts of compounds I can be converted in a manner known per se into other salts of compounds I; acid addition salts can be converted, for example, into other acid addition salts, for example by treatment of a salt of an inorganic acid, such as a hydrochloride, with a suitable metal salt, such as a sodium, barium or silver salt, of an acid, for example with silver acetate, in a suitable solvent in which an inorganic salt that forms, for example silver chloride, is insoluble and thus precipitates from the reaction mixture.

Depending upon the procedure and reaction conditions, compounds I having salt-forming properties can be obtained in free form or in the form of salts.

Owing to the close relationship between the compound I in free form and in the form of its salts, hereinabove and hereinbelow any reference to the free compound I or its salts should be understood as including also the corresponding salts or the free compound I, respectively, as appropriate and expedient The compounds I, including the salts of salt-forming compounds, can also be obtained in the form of their hydrates and/or may include other solvents, for example solvents that may have been used for the crystallisation of compounds in solid form.

Depending upon the starting materials and procedures chosen, the compounds I and their salts may be in the form of one of the possible isomers or in the form of a mixture thereof. There are obtainable as pure isomers, for example, pure diastereoisomers. Accordingly, mixtures of isomers may be in the form of, for example, mixtures of diastereoisomers. Isomeric mixtures of compounds I in free form or in salt form obtainable in accordance with the process or by another method can be separated into their components in customary manner, for example on the basis of the physicochemical differences between the constituents in known manner by fractional crystallisation, distillation an/or chromatography. Advantageously, the more active isomer is isolated.

The invention relates also to those forms of the process in which a compound obtainable as intermediate at any stage of the process is used as starting material and the remaining steps are carried out or a starring material is used in the form of a derivative or salt or, especially, is formed under the reaction conditions.

In the process of the present invention it is preferable to use those starting materials and intermediates, in each case in free form or in salt form, which result in the compounds I described at the beginning as being especially valuable or the salts thereof. The invention relates also to novel starting materials and intermediates, in each case in free form or in salt form, for the preparation of compounds I or the salts thereof, to the use thereof and to processes for their preparation, the variable R being as defined for compounds I.

The invention relates also to the use of compounds I and their pharmaceutically acceptable salts in the treatment of allergic conditions and diseases, preferably in the form of pharmaceutically acceptable preparations, especially in a method for the therapeutic treatment of the animal or human body, and to such a method of treatment.

The invention relates also to pharmaceutical compositions comprising as active ingredient a compound I or a pharmaceutically acceptable salt thereof, and to processes for their preparation. Those pharmaceutical compositions are, for example, for enteral, such as especially oral, also rectal, administration, for parenteral administration and for local administration to warm-blooded animals, especially humans, the compositions comprising the pharmacological active ingredient on its own or together with customary pharmaceutical excipients. The pharmaceutical compositions comprise (in percent by weight) for example from approximately 0.001% to 100%, preferably from approximately 0.1% to approximately 50%, active ingredient Pharmaceutical compositions for enteral or parenteral administration are, for example, those in unit dose forms, such as dragées, tablets, capsules or suppositories, and also ampoules. They are prepared in a manner known per se, for example by means of conventional mixing, granulating, confectioning, dissolving or lyophilising procedures. For example, pharmaceutical compositions for oral administration can be obtained by combining the active ingredient with solid carriers, if desired granulating a resulting mixture, and processing the mixture or granules, if desired or necessary after the addition of appropriate excipients, into tablets or dragée cores.

Suitable carriers are especially fillers, such as sugars, for example lactose, saccharose, mannitol or sorbitol, cellulose preparations and/or calcium phosphates, for example tricalcium phosphate or calcium hydrogen phosphate, and also binders, such as starch pastes using, for example, corn, wheat, rice or potato starch, gelatin, tragacanth, methylcellulose and/or polyvinylpyrrolidone, and, if desired, disintegrators, such as the above-mentioned starches, also carboxymethyl starch, crosslinked polyvinylpyrrolidone, agar or alginic acid or a salt thereof, such as sodium alginate. Excipients are especially flow conditioners and lubricants, for example silicic acid, talc, stearic acid or salts thereof, such as magnesium or calcium stearate, and/or polyethylene glycol. Dragée cores are provided with suitable, optionally enteric, coatings, there being used, inter alia, concentrated sugar solutions which may comprise gum arabic, talc, polyvinylpyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropylmethylcellulose phthalate. Dyes or pigments may be added to the tablets or dragée coatings, for example for identification purposes or to indicate different doses of active ingredient.

Further orally administrable pharmaceutical compositions are dry-filled capsules consisting of gelatin, and also soft, sealed capsules consisting of gelatin and a plasticiser, such as glycerol or sorbitol. The dry-filled capsules may comprise the active ingredient in the form of granules, for example in admixture with fillers, such as lactose, binders, such as starches, and/or glidants, such as talc or magnesium stearate, and optionally stabilisers. In soft capsules, the active ingredient is preferably dissolved or suspended in suitable liquids, such as fatty oils, paraffin oil or liquid polyethylene glycols, to which stabilisers may also have been added.

Suitable rectally administrable pharmaceutical compositions are, for example, suppositories that consist of a combination of the active ingredient with a suppository base material. Suitable suppository base materials are, for example, natural or synthetic triglycerides, paraffin hydrocarbons, polyethylene glycols or higher alkanols. It is also possible to use gelatin rectal capsules which comprise a combination of the active ingredient with a base material. Suitable base materials are, for example, liquid triglycerides, polyethylene glycols or paraffin hydrocarbons.

For parenteral administration there are suitable, especially, aqueous solutions of an active ingredient in water-soluble form, for example in the form of a water-soluble salt, and also suspensions of the active ingredient, such as corresponding oily injection suspensions, there being used suitable lipophilic solvents or vehicles, such as fatty oils, for example sesame oil, or synthetic fatty acid esters, for example ethyl oleate or triglycerides, or aqueous injection suspensions which comprise viscosity-increasing substances, for example sodium carboxymethylcellulose, sorbitol and/or dextran, and optionally also stabilisers.

Pharmaceutical compositions for local administration are, for example for topical treatment of the skin, lotions, creams and ointments, i.e. liquid or semi-solid oil-in-water or water-in-oil emulsions, fatty ointments, which are anhydrous, pastes, i.e. creams and ointments having secretion-absorbing powder constituents, gels, which are aqueous, of low water content or anhydrous and consist of swellable, gel-forming materials, foams, i.e. liquid oil-in-water emulsions in aerosol form which are administered from pressurised containers, and tinctures having an aqueous-ethanolic base and may comprise other customary pharmaceutical excipients, such as preservatives. The pharmaceutical compositions for local administration are prepared in a manner known per se by mixing the active ingredient with the pharmaceutical excipients, for example by dissolving or suspending the active ingredient in the base or in a portion thereof, if necessary. In order to prepare emulsions in which the active ingredient is dissolved in one of the liquid phases, the active ingredient is generally dissolved therein prior to emulsification; in order to prepare suspensions in which the active ingredient is suspended in the emulsion, the active ingredient is mixed with a portion of the base after emulsification and then added to the remainder of the formulation.

The dosage of the active ingredient can depend upon various factors, such as the effectiveness and duration of action of the active ingredient, the severity of the disease to be treated and of its symptoms, the mode of administration, the species of warm-blooded animal, and the sex, age, weight and(or individual condition of the warm-blooded animal. In a normal case, the, for example oral, daily dose for a warm-blooded animal weighing approximately 75 kg is estimated to be from approximately 1 mg to approximately 1000 mg, especially from approximately 5 mg to approximately 200 mg. It can be administered, for example, as a single dose or in several part doses of, for example, from 10 to 100 mg.

The following Examples are intended to illustrate the invention described hereinbefore, but without limiting the invention thereto. (Hereinbefore and hereinafter, unless otherwise indicated the meanings of the following abbreviations are: M.p.:=melting point; $CDCl_3$, deuterochloroform; DMSO-$d_6$=hexadeuterodimethyl sulfoxide; $CD_3OD$= deuteromethanol).

EXAMPLE 1

5-Phenyl-7H-pyrrolo[2,3-d]pyrimidin-4-yl-amine 4.3 g of N-[3-cyano-4-(4-methoxy-phenyl)-1H-pyrrol-2-yl]-formamidine are suspended in 150 ml of ethanol, and 0.3 g of sodium ethanolate is added. The reaction mixture is stirred under reflux for 1 hour and cooled to room temperature, and the product is filtered off. M.p.: 260–261° C.

a) N-(2-Oxo-2-phenyl-ethyl)-acetamide: 25.0 g of phenacylamine hydrochloride, 40.5 ml of triethylamine and 27.6 ml of acetic anhydride are suspended in 150 ml of tetrahydrofuran. Stirring is carried out at room temperature for 2.5 hours, followed by filtration, and the tetra-hydrofuran is removed using a rotary evaporator. The residue is crystallised from diethyl ether. M.p.: 95–96° C.

b) 2-Amino-4-phenyl-1H-pyrrole-3-carbonitrile: 0.9 g of sodium is dissolved in 100 ml of ethanol, and 2.6 g of malonic acid dinitrile are added thereto. Stirring is carried out for 30 minutes at 55° C.; 7.0 g of N-(2-oxo-2-phenyl-ethyl)-acetamide are then added thereto and stirring is carried out for 2 hours at 55° C. The reaction mixture is poured onto ice and the product is filtered off. $^1$H-NMR (DMSO-$d_6$, ppm): 10.4 (s, 1H), 7.6–7.1 (m, 5H), 6.62 (s, 1H), 5.75 (s, 2H).

c) N-[3-Cyano-4-(4-methoxy-phenyl)-1H-pyrrol-2-yl]-formamidine: 6.0 g of 2-amino-4-phenyl-1H-pyrrole-3-carbonitrile are dissolved in 80 ml of triethyl orthoformate, and the solution is stirred for 1 hour at 140° C. The triethyl orthoformate is removed under a high vacuum and the residue is dissolved in methanol saturated with ammonia. Stirring is carried out for 24 hours at room temperature, followed by filtration. The product is recrystallised from ethanol. M.p.: 238–239° C.

EXAMPLE 2

5-(3-Methoxy-phenyl)-7H-pyrrolo[2,3-d]pyrimidin-4-yl-amine 0.43 g of sodium ethanolate is dissolved in 100 ml of ethanol, and 5.0 g of N-[3-cyano4-(3-methoxy-phenyl)-1H-pyrrol-2-yl]formamidine are added thereto. Stirring is carried out under reflux for 1 hour; on cooling to room temperature, the product precipitates and is filtered off. M.p.: 249–250° C.

a) 2-Bromo-1-(3-methoxy-phenyl)-ethanone: 10 ml of 3-methoxy-acetophenone are dissolved in 10 ml of diethyl ether, and the solution is cooled to 5° C.; 0.2 g of aluminium trichloride is added thereto and the mixture is stirred for 5 minutes at 50C. 3.9 ml of bromine are then added dropwise thereto at 0–5° C. and further stirring is carried out for 1 hour at 0–5° C. The reaction mixture is poured into ethyl acetate and washed with water, saturated ammonium chloride solution and saturated sodium chloride solution. The organic phase is dried over anhydrous sodium sulfate and the ethyl acetate is removed using a rotary evaporator. The product is crystallised from ether/petroleum ether. M.p.: 64–65° C.

b) 2-Azido-1-(3-methoxy-phenyl)-ethanone: 12.0 g of 2-bromo-1-(4-methoxy-phenyl)-ethanone and 1.0 g of tricaprylmethylammonium chloride (aliquot 366) are placed in 300 ml of toluene, and a solution of 13.6 g of sodium azide in 40 ml of water is added dropwise thereto. The reaction mixture is stirred for 1.5 hours at 50–55° C. and then cooled to room temperature. The aqueous phase is separated off and extracted with toluene. The organic phases are combined, washed with water and dried, and the solvent is removed using a rotary evaporator. Flash chromatography using diethyl ether/petroleum ether as eluant yields the product in the form of an oil, $^1$H-NMR (CDCl$_3$, ppm):7.5–7.1 (m, 4H), 4.55 (s, 2H), 3.9 (s, 3H).

c) 2-Amino-1-(3-methoxy-phenyl)ethanone hydrochloride: 7.7 g of 2-azido-1-(4-methoxy-phenyl)-ethanone and 12 ml of 4N hydrochloric acid are dissolved in 150 ml of methanol, and the solution is hydrogenated over 1.5 g of palladium-on-carbon (10%) for 1 hour at normal pressure. The hydrogenation solution is filtered and the filtrate is concentrated by evaporation. $^1$H-NMR (DMSO-$d_6$, ppm): 8.5 (s, broad), 2H), 7.6–7.3 (m, 4H), 4.5 (q, 2H), 3.8 (s, 3H).

d) N-2-[2-(3-Methoxy-phenyl)-2-oxo-ethyl]acetamide: 7.60 g of 2-amino-1-(3-methoxy-phenyl)ethanone hydrochloride, 10.5 ml of triethylamine and 7.1 ml of acetic anhydride are suspended in 60 ml of tetrahydrofuran and the suspension is stirred for 2 hours at room temperature. The suspension is filtered and the filtrate is concentrated by evaporation. The residue is taken up in ethyl acetate and washed with water. The organic phase is dried over sodium sulfate and the solvent is removed using a rotary evaporator. This yields a crystalline residue which is stirred with ether. M.p.: 109–110° C.

e) 2-Amino4-(3-methoxy-phenyl)-1H-pyrrole-3-carbonitrile: 0.71 g of sodium is dissolved in 100 ml of ethanol, and 2.03 g of malonic acid dinitrile are added thereto. Stirring is carried out for 30 minutes at 55° C.; 6.38 g of N-2-[2-(3-methoxy-phenyl)-2-oxo-ethyl]acetamide are then added thereto and stirring is carried out for a further 2 hours at 55° C. The reaction mixture is poured onto ice and the product is filtered off. M.p.:117–119° C.

f) N-[3-Cyano-4-(3-methoxy-phenyl)-1H-pyrrol-2-yl] formamidine: 5.30 g of 2-amino4-(3-methoxy-phenyl)-1H-pyrrole-3-carbonitrile are dissolved in 50 ml of triethyl orthoformate, and the solution is stirred for 1 hour at 140° C. The triethyl orthoformate is removed under a high vacuum and the residue is dissolved in methanol saturated with ammonia. Stirring is carried out for 20 hours at room temperature, followed by filtration. The product is recrystallised from ethanol. M.p.: 188–190° C.

EXAMPLE 3

5-(4-Benzyloxy-phenyl)-7H-pyrrolo[2,3-d]pyrmidin-4-yl-amine 15.2 g of 2-amino-4-(4-benzyloxy-phenyl)-1H-pyrrole-3-carbonitrile are dissolved in 200 ml of triethyl orthoformate, and the solution is stirred for 1 hour at 140° C. The triethyl orthoformate is concentrated by evaporation under a high vacuum and the residue is dissolved in 500 ml of methanol saturated with ammonia. Stirring is carried out for 20 hours at room temperature. The suspension is filtered and the violet crystals are washed intensively with methanol. M.p.: 220° C. (decomposition).

a) 1-[4-(Benzyloxy)phenyl]ethanone: 48 ml of benzyl bromide are added dropwise to a suspension of 50.0 g of 4-hydroxyacetophenone and 76.0 g of potassium carbonate in 600 ml of acetone. Stirring is carried out under reflux for 20 hours. The reaction mixture is filtered, the filtrate is concentrated by evaporation and the residue is digested with petroleum ether. $^1$H-NMR (CDCl$_3$, ppm): 7.55 (m, 2H), 7.46 (m, 6H), 7.17 (ddd, 1H), 5.11 (s, 2H), 2.57 (s, 3H).

b) 2-Bromo-1-(4-benzyloxy-phenyl)-ethanone: 173 g of copper(II) bromide are suspended in 580 ml of ethyl acetate, and the suspension is heated to reflux temperature. A solution of 1-[4-(benzyloxy)phenyl]ethanone in 330 ml of chloroform is then added dropwise thereto over the course of 40 minutes. Stirring is carried out under reflux for 2 hours. The suspension is cooled to room temperature and filtered. The filtrate is concentrated by evaporation and the product is purified by flash chromatography (dichloromethane/ petroleum ether 1:1). M.p.: 58–59° C.

c) 2-Amino-1-(4-benzyloxy-phenyl)ethanone hydrochloride: 50.0 g of 2-bromo-1-(4-benzyloxy-phenyl)-ethanone are dissolved in 1 liter of chloroform, and 35 g of hexamethylenetetraamine are added. Stirring is carried out at room temperature for 20 hours. The product is filtered off and dissolved in 300 ml of ethanol/100 ml of conc. hydrochloric acid, and stirring is carried out under reflux for 2 hours. The reaction mixture is cooled to room temperature and the product is filtered off. M.p.: 237–240° C. (decomposition).

d) N-2-[2-(4-Benzyloxy-phenyl)-2oxo-ethyl]acetamide: 28.2 g of 2-amino-1-(4-benzyloxy-phenyl)ethanone hydrochloride are suspended in 300 ml of tetrahydrofuran, and 28.2 ml of triethylamine and 11.5 ml of acetic anhydride are added thereto. The reaction mixture is stirred for 3 hours at room temperature and filtered, and the mother liquor is concentrated by evaporation using a rotary evaporator. The residue is precipitated from diethyl ether with petroleum ether. $^1$H-NMR (CDCl$_3$, ppm): 7.8 (d, 2H), 7.4 (m, 5H), 7.02 (d, 2H), 6.6 (t, 1H), 5.18 (s, 2H), 4.7 (d, 2H), 2.1 (s, 3H).

e) 2-Amino-4-(4-benzyloxy-phenyl)-1H-pyrrole-3-carbonitrile: 1.5 g of sodium are dissolved in 300 ml of ethanol, and 4.5 g of malonic acid dinitrile are added thereto. Stirring is carried out for 30 minutes at 40° C.; 16.1 g of N-2-[2-(4-benzyloxy-phenyl)-2-oxo-ethyl]acetamide are then added thereto, and stirring is carried out for a further 18 hours at 40° C. The reaction mixture is cooled to room temperature and the product is filtered. $^1$H-NMR (DMSO-d$_6$, ppm): 10.3 (s, 1H), 7.48 (d, 2H), 7.35 (m, 5H), 7.0 (d, 2H), 6.4 (s, 1 H), 5.7 (s, 2H), 5.1 (s, 2H).

The corresponding pyrrolopyrimidines are prepared analogously to the above Examples, starting from suitably substituted acetophenone derivatives:

EXAMPLE 4

5-(4-Methoxy-phenyl)-7H-pyrrolo[2,3-d]pyrimidin-4-yl-amine, m.p.: 278–281° C.

EXAMPLE 5

5-(3-Benzyloxy-phenyl)-7H-pyrrolo[2,3-d]pyrimidin-4-yl-amine. m.p.: 241–243° C.

EXAMPLE 6

5-(3-Fluoro-pheny))-7H-pyrrolo[2,3-d]pyrimidin-4-yl-amine

EXAMPLE 7

5-(4-Fluoro-phenyl)-7H-pyrrolo[2,3-d]pyrimidin-4-yl-amine

EXAMPLE 8

5-(3-Chloro-phenyl)-7H-pyrrolo[2,3-d]pyrimidin-4-yl-amine

EXAMPLE 9

5-(4-Chloro-phenyl)-7H-pyrrolo[2,3-d]pyrimidin-4-yl-amine

EXAMPLE 10

5-(3-Bromo-phenyl)-7H-pyrrolo[2,3-d]pyrimidin-4-yl-amine

EXAMPLE 11

5-(4-Bromo-phenyl)-7H-pyrrolo[2,3-d]pyrimidin-4-yl-amine

EXAMPLE 12

5-p-Tolyl-7H-pyrrolo[2,3-d]pyrimidin-4-yl-amine

EXAMPLE 13

5-m-Tolyl-7H-pyrrolo[2,3-d]pyrimidin-4-yl-amine

EXAMPLE 14

5-(4-Trifluoromethyl-phenyl)-7H-pyrrolo[2,3-d]pyrimidin-4-yl-amine

EXAMPLE 15

5-(3-Trifluoromethyl-phenyl)-7H-pyrrolo[2,3-d]pyrimidin-4-yl-amine (2R/4S)-4-(Tolyl-4-sulfonyloxy)-pyrrolidine-1,2-dicarboxylic acid 1-tert-butyl ester 2-ethyl ester and (2R/

4R)-4-(tolyl-4-sulfonyloxy)-pyrrolidine-1,2-dicarboxylic acid 1-tert-butyl ester 2-ethyl ester are prepared according to G. L Baker et al., *J. Org. Chem.* (1981), 46, 2954.

EXAMPLE 16
(2R/4S)-4-4-Amino-5-phenyl-pyrrolo[2,3-d]pyrimidin-7-yl-pyrrolidine-1,2di-carboxylic acid 1-tert-butyl ester 2-ethyl ester 0.540 g of 5-phenyl-7H-pyrrolo[2,3-d]pyrimidin-4-yl-amine, 0.70 g of potassium carbonate and 0.670 g of 1 8-crown-6 ether are suspended in 5 ml of dimethylformamide, and stirring is carried out for 15 minutes at 70° C. 0.420 g of (2R/4R)-(tolyl-4-sulfonyloxy)-pyrrolidine-1,2dicarboxylic acid 1-tert-butyl ester 2-ethyl ester is then added thereto, and the mixture is stirred for a further 6 hours at 70° C. The reaction mixture is cooled to room temperature, filtered and then taken up in ethyl acetate. The ethyl acetate solution is washed three times with water and dried over sodium sulfate, and the solvent is removed using a rotary evaporator. The residue is purified by flash chromatography (ethyl acetate/petroleum ether 10:1). $^1$H-NMR (CDCl$_3$, ppm): 8.30 (s, 1H), 7.50 –7.30 (m, 5H), 6.95 (s, 1H), 5.5 (m, 1H), 5.22 (s, 2H), 4.62–4.42 (m, 1H), 4.24 (q, 2H), 4.12–3.80 (m, 2H), 2.75 (m, 1H), 2.50 (m, 1H), 1.48 (s, 9H), 1.30 (t, 3H).

EXAMPLE 17
(2R/4S)-4-(4-Amino-5-phenyl-pyrrolo[2,3-d]pyrimidin-7-yl)-pyrrolidine-2-carboxylic acid ethyl ester 0.500 g of (2R/4S)-4-(4-amino-5-phenyl-pyrrolo[2,3-d]pyrimidin-7-yl)-pyrrolidine-1,2-dicarboxylic acid 1-tert-butyl ester 2-ethyl ester (Example 16) is dissolved in 5 ml of absolute tetrahydrofuran; 15 ml of 4M hydrogen chloride in diethyl ether are added, and stirring is carried out at room temperature for 3 hours. The product is filtered off and dried under a high vacuum to yield the dihydrochloride of the title compound. M.p.: 176 –78° C.

EXAMPLE 18
(2R/4S )-4-(4-Amino-5-phenyl-pyrrolo[2,3-d]pyrimidin-7-yl)-pyrrolidine-2-hydroxymethyl-pyrrolidine-1-carboxylic acid tert-butyl ester 0.200 g of (2R/4S)4-(4-amino5-phenyl-pyrrolo[2,3-d]pyrimidin-7-yl)-pyrrolidine-1,2-dicarboxylic acid 1-tert-butyl ester 2-ethyl ester (Example 16) is dissolved in 15 ml of diethyl ether, and the solution is cooled to 0° C. 0.03 ml of methanol and 0.015 g of lithium borohydride are then added thereto, and stirring is carried out under reflux for 2 hours. Saturated ammonium chloride solution is added to the reaction mixture and extraction with ethyl acetate is carried out. The organic phase is separated off and dried over sodium sulfate, and the solvent is removed using a rotary evaporator. The residue is purified by flash chromatography (dichloromethane/methanol 10:0.4). $^1$H-NMR (CDCl$_3$, ppm): 8.31 (s, 1H), 7.5 (m, 5H), 6.92 (s, 1H), 5.5 (m, 1 H), 5.20 (s, 2H), 4.3 (m, 1H), 3.9 (m, 1H), 3.8 (m, 1H), 2.5 (m, 1H), 2.22 (m, 1H), 1.88 (s (broad), 1H), 1.48 (s, 9H).

EXAMPLE 19
(2R/4S)-[4-(4-Amino-5-phenyl-pyrrolo[2,3-d]pyrimidin-7-yl)-pyrrolidin-2-yl]-methanol 0.080 g of (2R/4S)4-(4-amino-5-phenyl-pyrrolo[2,3-d]pyrimidin-7-yl)-pyrrolidine-2-hydroxy-methyl-pyrrolidine-1-carboxylic acid tert-butyl ester (Example 18) is dissolved in 1 ml of tetrahydrofuran; 8 ml of 4M hydrogen chloride in diethyl ether are added, and stirring is carried out for 2 hours at room temperature. The product is filtered off and dried under a high vacuum to yield the dihydrochloride of the title compound. $^1$H-NMR (DMSO-d$_6$, ppm): 8.42 (s, 1H), 7.88 (s, 1H), 7.50 (m, 5H), 5.52 (m, 1H), 4.05 (m, 1H), 3.75 (m, 1H), 3.58 (m, 1H), 2.52 (m, 1H), 2.41 (m, 1H).

EXAMPLE 20
(2R/4S)-4-[4-Amino-5-(4-hydroxy-phenyl)-pyrrolo[2,3-d]pyrimidin-7-yl]-pyrrolidine-1,2-dicarboxylic acid 1-tert-butyl ester 2-ethyl ester 0.050 g of (2R/4S)4-[4amino-5-(4-benzyloxy-phenyl)-pyrrolo[2,3-d]pyrimidin-7-yl]-pyrrolidine-1,2-dicarboxylic acid 1-tert-butyl ester 2-ethyl ester is dissolved in 5 ml of methanol, and the solution is hydrogenated over 0.010 g of palladium-on-carbon (10%) for 18 hours at normal pressure. The catalyst is removed by filtration, the filtrate is concentrated by evaporation and the residue is purified by flash chromatography (dichloromethane/methanol 10:0.4). $^1$H-NMR (CDCl$_3$, ppm): 8.32 (s, 1H), 7.32 –7.25 (m, 3H), 6.95 (d, 2H), 6.88 (d, 1H), 5.5 (m, 1H), 5.20 (s, 2H), 4.62–4.48 (m, 1H), 4.25 (m, 3H), 4.19 (m, 1H), 2.75 (m, 1H), 2.52 (m, 1H), 1.48 (s, 9H), 1.25 (t, 3H).

a) (2R/4S)-4-[4-Amino-5-(4-benzyloxy-phenyl)-pyrrolo[2,3-d]pyrimidin-7-yl]-pyrrolidine-1,2-dicarboxylic acid 1-tert-butyl ester 2-ethyl ester. Prepared analogously to Example 16 from 5-(4-benzyloxy-phenyl)-7H-pyrrolo[2,3-d]pyrimidin-4-yl-amine (Example 3) and (2R/4R)-4-(tolyl-4-sulfonyloxy)-pyrrolidine-1,2-dicarboxylic acid 1-tert-butyl ester 2-ethyl ester. $^1$H-NMR (CDCl$_3$, ppm): 8.30 (s, 1H), 7.50 –7.35 (m, 7H), 7.08 (d. 2H), 6.89 (d, 1H), 5.50 (m, 1H), 5.18 (s, 2H), 5.11 (s, 2H), 5.60–5.42 (m, 1H), 4.25 ( q, 2H), 4.12 (m, 1H), 3.96 –3.75 (m, 1H), 2.75 (m, 1H), 2.50 (m, 1H), 1.49 (s, 9H), 1.28 (t, 3H).

EXAMPLE 21
(2R/4S)4-[4-Amino-5-(4-hydroxy-phenyl)-pyrrolo[2,3-d]pyrimidin-7-yl-pyrrolidine-2-carboxylic acid ethyl ester 0.183 g of (2R/4S)-4-[4-amino-5-(4-hydroxy-phenyl)-pyrrolo[2,3-]pyrimidin-7-yl]-pyrrolidine-1,2-dicarboxylic acid 1-tert-butyl ester 2-ethyl ester is dissolved in 3 ml of tetrahydrofuran; 20 ml of 4M hydrogen chloride in diethyl ether are added thereto, and stirring is carried out for 16 hours at room temperature. The resulting suspension is filtered and the product is washed with diethyl ether. The dihydrochloride of the title compound is obtained. $^1$H-NMR (DMSO-d$_6$, ppm): 9.8 (s (broad), 1H), 8.5 (s, 1H), 7.9 (s, 1H), 7.3 (d. 2H), 6.9 (d; 2H), 5.6 (m, 1H), 4.9 (dd, 1H), 4.29 (q, 2H), 3.9 (m, 1H), 3.60 (m, 1H), 2.70 (m, 2H). 1.28 (t, 3H).

EXAMPLE 22
(2R/4S)-4-[4-Amino-5-(4-hydroxy-phenyl)-pyrrolo[2,3-d]pyrimidin-7-yl-2-hydroxymethyl-pyrrolidine-1-carboxylic acid tert-butyl ester Prepared analogously to Example 20 starring from (2R/4S)+[4-amino-5-(4-benzyloxy-phenyl)-pyrrolo[2,3-d]pyrimidin-7-yl-2-hydroxymethyl-pyrrolidine-1-carboxylic acid tert-butyl ester. $^1$H-NMR (CDCl$_3$, ppm): 10.5 (s, 1H), 8.3 (s, 1H), 7.3 (d, 2H), 6.95 (d, 2H), 6.85 (s, 1H), 5.58 (m,1H), 5.22 (s, 2H), 4.28 (m,$_1$H), 4.0–3.62 (m, 4H), 2.5 (m,$_1$H), 2.22 (m, 1H), 1.5 (s, 9H).

a) (2R/4S)-4-[4-Amino-5-(4-benzyloxy-phenyl)-pyrrolo[2,3-d]pyrimidin-7-yl-2-hydroxymethyl-pyrrolidine-1-carboxylic acid tert-butyl ester prepared analogously to Example 18 starting from (2R/4S)-4-[4-amino-5-(4-benzyloxy-phenyl)-pyrrolo[2,3-d]pyrimidin-7-yl]pyrrolidine-1,2-dicarboxylic acid 1-tert-butyl ester 2-ethyl ester (Example 20a). $^1$H-NMR (CDCl$_3$, ppm): 8.32 (s, 1H), 7.5–7.3 (m, 7H), 7.1 (d, 2H), 6.9 (s, 1H), 5.5 (m,$_1$H), 5.12 (s, 2H), 4.25 (m,$_1$H), 3.98 –3.70 (m, 4H), 2.5 (m, 1H), 2.2 (m, 1H), 1.5 (s, 9H).

EXAMPLE 23

(2R/4S)-4-[4-Amino-7-(5-hydroxymethyl)-pyrrolidin-3-yl)-H-pyrrolo[2,3-d]pyrimidin-5-yl]-phenol 0.034 g of (2R/4S)-4-[4-amino-5-(4-benzyloxy-phenyl)-pyrrolo[2,3-d]pyrimidin-7-yl-pyrrolidine-2-carboxylic acid ethyl ester is dissolved in 5 ml of methanol, and the solution is hydrogenated over 0.010 g of palladium-on-carbon (10%) for 17 hours at normal pressure. The catalyst is removed by filtration, the filtrate is concentrated by evaporation and the residue is solidified with diethyl ether. $^1$H-NMR (CD$_3$OD, ppm): 8.38 (s, 1H), 7.52 (s, 1H), 7.32 (d, 2H), 6.92 (d, 2H), 5.62 (m,$_1$ I H), 4.30 (m, 1H), 4.00–3.88 (m, 4H), 2.60 (m, 2H).

a) (2P/4S)-4-[4-Amino-5-(4-benzyloxy-phenyl)pyrrolo[2,3-d]pyrimidin-7-yl]-2-hydroxymethyl-pyrrolidine-1-carboxylic acid tert-butyl ester prepared analogously to Example 18 starting from (2R/4S)-4-[4-amino-5-(4-benzyloxy-phenyl)-pyrrolo[2,3-d]pyrimidin-7-yl]-pyrrolidine-1,2-dicarboxylic acid 1-tert-butyl ester 2-ethyl ester (Example 20a). $^1$H-NMR (CDCl$_3$, ppm): 8.52 (s, 1H), 7.52–7.32 (m, 7H), 7.1 (d, 2H), 6.95 (d,$_1$H), 5.50 (m, 1H), 5.13 (s, 2H), 4.62–4.42 (m, 2H), 4.28 (m, 2H), 4.10 (m, 1H), 3.95–3.70 (m, 1H), 2.75 (m, 1H), 2.50 (m, 1H),1.49 (s, 9H).

b) (2R/4S)-{4-[4-Amino-5-(4-benzyloxy-phenyl)-pyrrolo[2,3-d]pyrimidin-7-yl]-pyrrolidin-2-yl}-methanol: 0.100 g of (2R/4S)4-[4-amino-5-(4-benzyloxy-phenyl)-pyrrolo[2,3-d]pyrimidin-7-yl]-pyrrolidine-1,2-dicarboxylic acid 1-tert-butyl ester is dissolved in 4 ml of tetrahydrofuran; 10 ml of 4M hydrogen chloride in diethyl ether are added, and stirring is carried out for 1 hour at room temperature. The product is filtered off and dried under a high vacuum. The dihydrochloride of the title compound is obtained. $^1$H-NMR (CD$_3$OD, ppm): 8.4 (s, 1H); 7.60 (s, 1H), 7.5–7.10 (m, 9H), 5.65 (m, 1H), 5.18 (s, 2H), 4.32 (m, 1H), 4.00–3.65 (m, 4H), 2.60 (m, 2H).

EXAMPLE 24

(2R/4S)-4-(4-Amino-5-phenyl-pyrrolo[2,3-d]pyrimidin-7-yl)-1-(2,2-dimethyl-propionyl)-pyrrolidine-2-carboxylic acid ethyl ester 0.130 g of (2R/4S)-4-(4-benzyloxycarbonylamino-5-phenyl-pyrrolo[2,3-d]pyrimidin-7-yl)-1-(2,2-dimethyl-propionyl)-pyrrolidine-2-carboxylic acid ethyl ester is dissolved in 8 ml of methanol, and the solution is hydrogenated over 0.030 g of palladium-on-carbon (10%) for 1 hour at normal pressure. The catalyst is removed by filtration, the filtrate is concentrated by evaporation and the residue is purified by flash chromatography (dichloromethane/methanol 10:0.4). $^1$H-NMR (DMSO-d$_6$, ppm): 8.2 (s, 1H), 7.55–7.30 (m, 6H), 6.15 (s (broad), 2H), 5.99 (m, 1H), 4.62 (m, 1H), 4.30–3.98 (m, 4H), 2.78 (m, 1H), 2.30 (m, 1H), 1.22 (t, 3H), 1.10 (m, 9H).

a) (2R/4S)-4-(4Benzyloxycarbonylamino-5-phenyl-pyrrolo[2,3-d]pyrmidin-7-yl)-pyrrolidine-1,2-dicarboxylic acid 1-tert-butyl ester 2-ethyl ester 1.51 g of benzoxycarbonylimidazolide (Z-imidazole) are dissolved in 30 ml of dichloromethane, and the solution is cooled to 0° C.; 1.41 g of triethyloxonium tetrafluoroborate are then added thereto, and stirring is carried out for 1 hour at 0° C. and for 3 hours at room temperature. 0.560 g of (2R/4S)-4-(4-amino-5-phenyl-pyrrolo[2,3-d]pyrimidin-7-yl)-pyrrolidine-1,2-dicarboxylic acid 1-tert-butyl ester 2-ethyl ester (Example 16) is then added thereto, and stirring is carried out for 20 hours at room temperature. The reaction mixture is taken up in 150 ml of dichloromethane and extracted twice with saturated sodium hydrogen sulfate solution, twice with water and once with saturated sodium chloride solution. The organic phase is dried over sodium sulfate and filtered, and the solvent is removed using a rotary evaporator. The residue is purified by flash chromatography (diethyl ether/petroleum ether 8:2). $^1$H-NMR (CDCl$_3$, ppm): 8.70 (s, 1H), 7.50–7.32 (m, 10H), 7.23 (s, 1H), 5.55 (m, 1H), 5.08 (s, 2H), 4.48 (m, 1H), 4.25–4.10 (m, 3H), 3.80 (m, 1H), 2.97 (m, 1H), 2.40 (m,$_1$H), 1.45 (s, 9H), 1.22 (t, 3H). Z-Imidazole [CAS Reg. No.: 22129-07-3] is prepared from Z-chloride and imidazole according to B. E. Watkins, H. Rapoport, J. Org. Chem. (1982), 47, 4471–4477.

b) (2R/4S)-4-(4-Benzyloxycarbonyl-amino-5-phenyl-Pyrrolo[2,3 d]pyrimidin-7-yl)-pyrrolidine-2-carboxylic acid ethyl ester prepared analogously to Example 19 from (2R/4S)-4-(4-benzyloxycarbonylamino-5-phenyl-pyrrolo[2,3-d]pyrimidin-7-yl)-pyrrolidine-1,2-dicarboxylic acid 1-tert-butyl ester 2-ethyl ester. The hydrochloride of the title compound is obtained. $^1$H-NMR (DMSO-d$_6$, ppm): 8.28 (s, 1H), 8.00 (s, 1H), 7.60–7.30 (m, 1OH), 5.80 (m,$_1$H), 5.30 (s, 2H), 4.70 (m, 1H), 4.32 (m, 2H), 4.10–3.90 (m, 2H), 3.20 (m, 1H), 2.80 (m,1H), 1.32 (t, 3H).

c) (2R/4S)-4-(4-Benzyloxycarbonylamino-5-phenyl-pyrrolo[2,3-d]pyrimidin-7-yl)-1-(2,2-di-methyl-propionyl)-pyrrolidine-2-carboxylic acid ethyl ester: 0.250 g of (2R/4S)-4-(4-benzyl-oxycarbonyl-amino-5-phenyl-pyrrolo[2,3-d]pyrimidin-7-yl)-pyrrolidine-2-carboxylic acid ethyl ester hydrochloride is suspended in 4 ml of tetrahydrofuran/dimethylformamide (1:1); 0.140 ml of triethylamine and 0.06 ml of pivaloyl chloride are then added thereto. Stirring is carried out at room temperature for 3 hours. The reaction mixture is taken up in ethyl acetate and washed three times with water. The organic phase is dried over anhydrous sodium sulfate, the solvent is removed using a rotary evaporator and the residue is purified by flash chromatography (dichloromethane/methanol 10:0.2). $^1$H-NMR (CDCl$_3$, ppm): 8.75 (s, 1H), 7.52–7.31 (m, 10H), 7.09 (s, 1H), 5.65 (m, 1H), 5.10 (s, 2H), 4.80 (m, 1H), 4.40–4.20 (m, 2H), 4.12 (q, 2H), 2.75 (m, 1H), 2.45 (m,$_1$H), 1.30–1.18 (m, 12H).

Examples 25–29 are prepared analogously to Example 24:

EXAMPLE 25

(2R/4S)-4-(4-Amino-5-phenyl-pyrrolo[2,3-d]pyrimidin-7-3d)-1-(3,3-dimethyl-butyryl)-pyrrolidine-2-carboxylic acid ethyl ester $^1$H-NMR (CDCl$_3$, ppm): 8.28 (s, 1H), 7.5–7.35 (m, 5H), 6.9 (s, I H), 5.70 (s (broad), 2H), 5.55 (m,$_1$H), 4.80 (m, 1H), 4.3–4.2 (m, 3H), 3.90 (m,1H), 2.80 (m, 1H), 2.50 (m, 1H), 2.2 (q, 2H), 1.30 (t, 3H), 1.01 (s, 9H).

EXAMPLE 26

(2R/4S)-4-[4-Amino-5-(4-hydroxy-phenyl)-pyrrolo[2,3-d]pyrimidin-7-yl]-1-(3,3-dimethyl-butyryl)-pyrrolidine-2-carboxylic acid ethyl ester $^1$H-NMR (CDCl$_3$, ppm): 8.30 (s, 1H), 7.30 (d, 2H), 6.98 (d, 2H), 6.80 (s, 1H), 5.60 (m, 1H), 5.40 (s (broad), 2H), 4.80 (m, 1H), 4.30 (m, 3H), 3.95 (m, 1H), 2.80 (m, 1H), 2.55 (m, 1H), 2.22 (q, 2H), 1.30 (t, 3H), 1.02 (s, 9H).

EXAMPLE 27

(2R/4S)-4-(4-Amino-5-phenyl-pyrrolo[2,3-d]pyrimidin-7-yl)-1-tert-butoxyacetyl-pyrrolidine-2carboxylic acid ethyl ester $^1$H-NMR (CDCl$_3$, ppm): 8.3 (s, 1H), 7.5–7.35 (m, 5H), 7.0 (s, 1H), 5.55 (m, 1H), 5.10 (s, 2H), 4.75 (m, 1H), 4.32–4.00 (m, 6H), 2.78 (m,1H), 2.5 (m,1H), 1.28 (t, 3H), 1.10 (s, 9H).

EXAMPLE 28

(2R/4S)-4-(4-Amino-5-phenyl-pyrrolo[2,3-d]pyrimidin-7-yl)-1-(2-tert-butoxy-carbonylamino-3-methyl-pentanoyl)-pyrrolidine-2-carboxylic acid ethyl ester ¹H-NMR (CDCl₃, ppm): 8.30 (s, 1H), 7.50 –7.32 (m, 5H), 6.9 (s, 1H), 5.55 (m, 1H), 5.27 (m, 3H), 4.75 (m, 1H), 4.42–4.03 (m, 4H), 2.95 (m, 1H), 2.50 (m,1H), 1.48 (s, 9H), 1.39–1.28 (m, 5H), 1.10 (m, 1H), 0.9 (d, 3H), 0.8 (t, 3H).

EXAMPLE 29
(2R/4S)-1-(2-Amino-3-methyl-pentanoyl)-4-(4-amino-5-phenyl-pyrrolo[2,3-d]pyrimidin-7-yl)-pyrrolidine2-carboxylic acid ethyl ester ¹H-NMR (DMSO-d₆, ppm): 8.50 (s, 1H), 8.20 (s (broad), 2H), 7.80 (s, 1H), 7.50–7.35 (m, 5H), 5.55 (m, 1H), 4.72 (m, 1H), 4.38–3.90 (m, 4H), 3.00 (m, 1H), 2.50 (m, 1H), 1.25 (t, 3H), 1.0 (m, 1H), 0.90 (d, 3H), 0.70 (t, 3H).

EXAMPLE 30
(2R/4S)-1-[4-(4-Amino-5-phenyl-pyrrolo[2,3-d]pyrimidin-7-yl)-2-hydroxymethyl-pyrrolidin-1-yl]-2,2-dimethyl-propan-1-one Prepared analogously to Example 24 from (2R/4S)-{7-[1-(2,2-dimethyl-propionyl)-5-hydroxymethyl-pyrrolidin-3-yl-5-phenyl-7H-pyrrolo[2,3-d]pyrimidin-4-yl}-carbamic acid benzyl ester. ¹H-NMR (CDCl₃, ppm): 8.3 (s, 1H), 7.52–7.38 (m, 5H), 6.9 (s, 1H), 2H), 5.55 (m, 1H), 5.20 (s (broad), 4.75 (m, 1H), 4.18–3.70 (m, 4H), 2.60 (m,₁H), 2.25 (m,₁H), 1.70 (s (broad),1H), 1.00 (s, 9H).

a) (2R/4S)-{7-[1-(2,2-Dimethyl-propionyl)-5-hydroxymethyl-pyrrolidin-3-yl]-5-phenyl-7H-pyrrolo[2,3-d]pyrimidin-4-yl}carbamic acid benzyl ester: Prepared analogously to Example 18 from (2R/4S)-4-(4-benzyloxycathonylamino-5-phenyl-pyrrolo[2,3-d]pyrimidin-7-yl)-1-(2,2-dimethyl-propionyl)-pyrrolidine-1, 2-dicarboxylic acid 1-ethyl ester (Example 24c). ¹H-NMR (CDCl₃, ppm): 8.72 (s, 1H), 7.50–7.30 (m, 1OH), 7.02 (s, 1H), 5.59 (m, 1H), 5.08 (s, 2H), 4.75 (m, 1H), 4.20–3.70 (m, 4H), 2.51 (m, 1H), 2.25 (m, 1H), 1.75 (s (broad), 1H), 1.12 (s, 9H).

Examples 31–34 are prepared analogously to Example 30:

EXAMPLE 31
(2R/4S)-1-[4-(4-Amino-5-phenyl-pyrrolo[2,3-d]pyrimidin-7-yl)-2-hydroxymethyl-pyrrolidin-1-yl]-3,3-dimethyl-butan-1-one ¹H-NMR (CDCl₃, ppm): 8.30 (s, 1H), 7.5–7.34 (m, 5H), 6.97 (s,1H), 5.52 (m, 1H), 5.28 (s, 2H), 4.71 (m, 1H), 4.35 (m,1H), 4.10 (m, 1H), 3.95–3.70 (m, 2H), 2.60 (m, 1H), 2.30 (m, 1H), 2.20 (q, 2H), 1.02 (s, 9H).

EXAMPLE 32
(2R/4S)-1-{4-Amino-5-(4-hydroxy-phenyl)-pyrrolo[2,3-d]pyrimidin-7-yl]-2-hydroxymethyl-pyrrolidin-1-yl}-3-3-dimethyl-butan-1-one ¹H-NMR (CD₃OD, ppm): 8.15 (s, 1H), 7.30 (d, 2H), 7.15 (s, 1H), 6.88 (d, 2H), 5.51 (m, 1H), 4.50 (m, 1H), 4.10–3.60 (m, 4H), 2.70–2.50 (m, 2H), 2.25 (q, 2H), 0.99 (s, 9H).

EXAMPLE 33
(2R/4S)-1-[4-(4-Amino-5-phenyl-pyrrolo[2,3-d]pyrimidin-7-yl-2-hydroxymethyl-pyrrolidin-1-yl]-2- tert-butoxy-ethanone ¹H-NMR (CDCl₃, ppm): 8.70 (s, 1H), 7.50–7.40 (m, 5H), 7.10 (s, 1H), 5.58 (m, ₁H), 4.52 (m, 1H), 4.32 (m, 1H), 4.10 (m, 1H), 4.00 (m, 2H), 3.90 (m, 1H), 3.72 (m, 1H), 2.52 (m, 1H), 2.30 (m, 1H), 1.10 (s, 9H).

EXAMPLE 34
(2R/4S)-2-Amino-1-[4-(4-amino-5-phenyl-pyrrolo[2,3-d]pyrimidin-7-yl)-2-hydroxymethyl-pyrrolidin-1-yl]-3-methyl-pentan-1-one dihydrochloride ¹H-NMR (DMSO-d₆, ppm): 8.48 (s, 1H), 8.30 (s, 2H), 7.80 (s,1H), 7.50 (m, 5H), 5.70 (m, 1H), 4.38 (m,₁H), 4.20 (m,₁H), 3.90 (m,1H), 3.60 (m, 2H), 3.50 (m,₁H), 3.40 (m, ₁H), 2.70–2.52 (m, 2H), 1.40 (m,₁H), 1.10 (t, 3H), 0.80–0.68 (m, 5H).

EXAMPLE 35
(2R/4R )-4-(4-Amino-5-phenyl-pyrrolo[2,3-d]pyrimidin-7-yl-pyrrolidin-1,2-di carboxylic acid 1-tert-butyl ester 2-ethyl ester Prepared analogously to Example 16 from (2R/4S)-4-(tolyl-4-sulfonyloxy)-pyrrolidine-1,2-dicarboxylic acid 1-tert-butyl ester 2-ethyl ester and from 5-phenyl-7H-pyrrolo[2,3-d]pyrimidin-4-yl-amine (Example 1). ¹H-NMR (CDCl₃, ppm): 8.30 (s, 1H), 7.50–7.35 (m, 5H), 7.10 (s, 1H), 5.52 (m,1H), 5.20 (s, 2H), 4.45 (m,1H), 4.30–4.08 (m, 3H), 3.80 (m,₁H), 2.90 (m, 1H), 2.35 (m,₁H), 1.48 (s, 9H), 1.30 (t, 3H).

EXAMPLE 36
(2R/4R)-4-(4-Amino-5-phenyl-pyrrolo[2,3-d]pyrimidin-7-yl)-pyrrolidine-2-carboxylic acid ethyl ester Prepared analogously to Example 17 from (2R/4R)-4-(4-amino-5-phenyl-pyrrolo[2,3-d]pyrimidin-7-yl)-pyrrolidine-1,2-dicarboxylic acid 1-tert-butyl ester 2-ethyl ester (Example 35). ¹H-NMR (CD₃OD, ppm): 8.40 (s, 1H), 7.70 (s, 1H), 7.50–7.30 (m, 5H), 5.70 (m,₁H), 4.80 (m, 1H), 4.35 (q, 2H), 4.02–3.90 (m, 2H), 3.15 (m,₁H), 2.70 (m, 1H), 1.27 (t, 3H).

EXAMPLE 37
(2R/4R )-4-(4-Amino5-phenyl-pyrrolo[2,3-d]pyrimidin-7-yl)-pyrrolidine-2-hydroxymethyl-pyrrolidine-1-carboxylic acid tert-butyl ester Prepared analogously to Example 18 from (2R/4R)-4-(4-amino-5-phenyl-pyrrolo[2,3-d]pyrimidin-7-yl)-pyrrolidine-1,2-dicarboxylic acid 1-tert-butyl ester 2-ethyl ester (Example 35). ¹H-NMR (CDCl₃, ppm): 8.30 (s, 1H), 7.50–7.35 (m, 5H), 7.02 (s,1H), 5.30 (m, 1H), 5.17 (s, 2H), 4.20 (m, 2H), 3.85 (m, 1H), 3.75 (m, 1H), 3.60 (m,₁H), 2.65 (m, 1H), 2.20 (m, 1H), 1.48 (s, 9H).

EXAMPLE 38
(2R/4R)-[4-(4-Amino-5-phenyl-pyrrolo[2,3-d]pyrimidin-7-yl)-pyrrolidin-2-yl]-methanol Prepared analogously to Example 19 from (2R/4R)-4-(4-amino-5-phenyl-pyrrolo[2,3-d]-pyrimidin-7-yl)-pyrrolidine-2-hydroxymethyl-pyrrolidine-1-carboxylic acid tert-butyl ester (Example 37). ¹H-NMR (CD₃OD, ppm): 8.42 (s, 1H), 7.81 (s, 1H), 7.52–7.40 (m, 5H), 5.80 (m, 1H), 4.10–3.80 (m, 5H), 2.70 (m, 1H), 2.45 (m,1H).

EXAMPLE 39
(2R/4R)-4-[4-Amino-5-(4-hydroxy-phenyl)-pyrrolo[2,3-d]pyrimidin-7-yl]-pyrrolidine-1,2-dicarboxylic acid 1-tert-butyl ester 2-ethyl ester Prepared analogously to Example 20 from (2R/4S-4-(tolyl-4-sulfonyloxy)-pyrrolidine-1,2-dicarboxylic acid 1-tert-butyl ester 2-ethyl ester and from 5-(4-benzyloxy-phenyl)-7H-pyrrolo-[2,3-d]pyrimidin-4-yl-amine (Example 3). ¹H-NMR (CDCl₃, ppm): 8.30 (s, 1H), 7.3 (d, 2H), 7.03 (s, 1H), 6.92 (d, 2H), 5.49 (m, 1H), 5.19 (s, 2H), 4.45 (m, 1H), 4.28–4.02 (m, 3H), 3.75 (m, 1H), 2.90 (m, 1H), 2.35 (m, 1H), 1.48 (s, 9H), 1.22 (t, 3H).

EXAMPLE 40
(2R/4R)4-[4-Amino-5-(4-hydroxy-phenyl)-pyrrolo[2,3-d]pyrimidin-7-yl-pyrrolidine-2-carboxylic acid ethyl ester Prepared analogously to Example 21 from (2R/4R)-4-[4-amino-5-(4-hydroxy-phenyl)-pyrrolo-[2,3-d]pyrimidin-7-yl]-pyrrolidine-1,2-dicarboxylic acid I -tert-butyl ester 2-ethyl ester (Example 39). $^1$H-NMR (CD$_3$OD, ppm): 8.32 (s, 1H), 7.53 (s, 1H), 7.30 (d, 2H), 6.92 (d, 2H), 5.65 (m, 1H), 4.72 (m, 1H), 4.38 (m, 2H), 4.02–3.88 (m, 2H), 3.15 (m, 1H), 2.78 (m, 1H), 1.32 (t, 3H).

EXAMPLE 41

(2R/4R)-4-[4-Amino-5-(4-hydroxy-phenyl)-pyrrolo[2,3-d]pyrimidin-7-yl-2-hydroxymethyl-pyrrolidine-1-carboxylic acid tert-butyl ester Prepared analogously to Example 22 from (2R/4R)-4-[4-amino-5-(4-benzyloxy-phenyl)-pyrrolo[2,3-d]pyrimidin-7-yl]-pyrrolidine-1,2-dicarboxylic acid I -tert-butyl ester 2-ethyl ester. $^1$H-NMR (CD3OD, ppm): 8.12 (s, 1H), 7.32 (d, 2H), 7.30 (s, 1H), 6.98 (d, 2H), 5.22 (m, 1H), 4.15 (m, 1H), 4.03 (m, 1H), 3.85 (m, 1H), 3.70 (m, 1H), 3.50 (m, 1H), 2.75 (m, 1H), 2.40 (m, 1H), 1.50 (s, 9H).

EXAMPLE 42

(2R/4R)-4-[4-Amino-7-(5-hydroxymethyl)-pyrrolidin-3-yl)-7H-pyrrolo[2,3-d]pyrimidin-5-yl]-phenol Prepared analogously to Example 23 from (2R/4R)-4-[4-amino-5-(4-benzyloxy-phenyl)-pyrrolo[2,3-d]pyrimidin-7-yl-2-hydroxymethyl-pyrrolidine-1-carboxylic acid tert-butyl ester. $^1$H-NMR (CD$_3$OD, ppm): 8.32 (s, 1H), 7.62 (s, 1H), 7.30 (d, 2H), 6.92 (d, 2H), 5.65 (m, 1H), 4.02–3.80 (m, 2H), 2.80 (m, $_1$H), 2.45 (m, $_1$H).

EXAMPLE 43

(2R/4R)-4-(4-Amino-5-phenyl-pyrrolo[2,3-d]pyrimidin-7-yl)-1-(2,2-dimethyl-propionyl)-pyrrolidine-2-carboxylic acid ethyl ester Prepared analogously to Example 24 from (2R/4R)-4-(4-benzyloxycarbonylamino-5-phenyl-pyrrolo[2,3-d]pyrimidin-7-yl)-1-(2,2-dimethyl-propionyl)-pyrrolidine-2-carboxylic acid ethyl ester. $^1$H-NMR (CDCl$_3$, ppm): 8.22 (s, 1H), 7.60–7.40 (m, 5H), 7.33 (s, 1H), 5.52 (m, 1H), 4.68 (t, 1H), 4.50 (m, 1H), 4.20 (q, 2H), 3.98 (t, 1H), 2.90 (m, 1H), 2.31 (m, 1H), 1.30 (m, 12H).

EXAMPLE 44

(2R/4R)-1-[4-(4-Amino-5-phenyl-pyrrolo[2,3-d]pyrimidin-7-yl)-2-hydroxymethyl-pyrrolidin-1-yl-2,2-dimethyl-propan-1-one Prepared analogously to Example 30 from (2R/4R)-{7-[1-(2,2-dimethyl-propionyl)-5-hydroxymethyl-pyrrolidin-3-yl-5-phenyl-7H-pyrrolo[2,3-d]pyrimidin-4-yl}-carbamic acid benzyl ester. $^1$H-NMR (CDCl$_3$, ppm): 8.3 (s, 1H), 7.52–7.40 (m, 5H), 7.05 (s, 1H), 2H), 5.30 (s, 2H), 5.20 (m, 1H), 5.30 (s (broad), 2H), 4.50 (m, 2H), 3.90 (m, 1H), 3.75–3.65 (m, 2H), 2.70 (m, H), 2.20 (m, 1H), 1.30 (s, 9H).

EXAMPLE 45

3-(4-Amino-5-phenyl-pyrrolo[2,3-d]pyrimidin-7-yl)-pyrrolidine-1-carboxylic acid tert-butyl ester Prepared analogously to Example 16 from 5-phenyl-7H-pyrrolo[2,3-d]pyrimidin-4-yl-amine (Example 1) and 3-(tolyl-4-sulfonyloxy)-pyrrolidine-1-carboxylic acid tert-butyl ester [CAS Reg. No: 103057-45-0]. $^1$H-NMR (CDCl$_3$, ppm): 8.32 (s,1H), 7.51–7.35 (m, 5H), 6.99 (s, 1H), 5.50 (m, 1H), 5.18 (s, 2H), 3.98–3.40 (m, 4H), 2.49 (m, 1H), 2.25 (m, 1H), 1.45 (s, 9H).

EXAMPLE 46

5-Phenyl-7-pyrrolidin-3-yl-7H-pyrrolo[2,3-d]pyrimidin-4-yl-amine

Prepared analogously to Example 17 from 3-(4-amino-5-phenyl-pyrrolo[2,3-d]pyrimidin-7-yl)-pyrrolidine-1-carboxylic acid tert-butyl ester (Example 45). $^1$H-NMR (DMSO-d$_6$, ppm): 8.58 (s, 1H), 8.10 (s,1I H), 7.58–7.38 (m, 5H), 5.60 (m, 1H), 3.86–3.30 (m, 4H), 2.52 (m, 1H), 2.38 (m, 1H).

EXAMPLE 47

(2S/4R)-2-(4-Amino-5-phenyl-pyrrolo[2,3-d]pyrimidin-7-ylmethyl)-4-hydroxy-pyrrolidine-1-carboxylic acid tert-butyl ester Prepared analogously to Example 16 from 5-phenyl-7H-pyrrolo[2,3-d]pyrimidin-4-yl-amine (Example 1) and (2S/4R)-4-hydroxy-2-(tolyl-4-sulfonyloxymethyl)-pyrrolidine-1-carboxylic acid tert-butyl ester. $^1$H-NMR (CDCl$_3$, ppm): 8.30 (s, 1H), 7.50–7.38 (m, 5H), 6.92 (s, 1H), 5.12 (s, 2H), 4.60–4.32 (m, 4H), 4.10 (m, 1H), 3.60 (m, 1H), 3.40 (m, 1H), 1.49 (s, 9H). (2S/4R)4Hydroxy-2-(tolyl-4-sulfonyloxymethyl)-pyrrolidine-1-carboxylic acid tert-butyl ester is prepared according to T. Nakamura et al., *J. Org. Chem.* (1992), 57, 3783–3789.

EXAMPLE 48

(3R/5S)-5-(4-Amino-5-phenyl-pyrrolo[2,3-d]pyrimidin-7-ylmethyl)-pyrrolidin-3-ol

Prepared analogously to Example 17 from (2S,4R)-2-(4-amino-5-phenyl-pyrrolo[2,3-d]pyrimidin-7-ylmethyl)-4-hydroxy-pyrrolidine-1-carboxylic acid tert-butyl ester (Example 47). $^1$H-NMR (DMSO-d$_6$, ppm): 8.58 (s, 1H), 7.95 (s, 1H), 7.55 (m, 5H), 4.75 (m, 2H), 4.48 (m, 1H), 4.75 (m, 1H), 3.44 (m, 1H), 3.0 (m, 1H), 2.05 (m, 1H), 1.82 (m, 1H).

EXAMPLE 49

(2R/4R)-2-(4-Amino-5-phenyl-pyrrolo[2,3-d]pyrimidin-7-ylmethyl)-4-hydroxy-pyrrolidine-1-carboxylic acid tert-butyl ester Prepared analogously to Example 16 from 5-phenyl-7H-pyrrolo[2,3-d]pyrimidin-4-yl-amine (Example 1) and (2R/4R (tert-butyl-dimethyl-silanyloxy)-2-(tolyl-4-sulfonyloxymethyl)-pyrrolidine-1-carboxylic acid tert-butyl ester. $^1$H-NMR (CDCl$_3$, ppm): 8.31 (s, 1H), 7.52–7.32 (m, 5H), 7.10 (s, 1H), 5.22 (s, 2H), 4.80 (m,1H), 4.55 (m, 2H), 4.30 (m, 2H), 3.60 (m, 1H), 3.48 (m, 1H), 1.49 (s, 9H).

(2R/4R)-4-Hydroxy-2-(tolyl-4-sulfonyloxymethyl)-pyrrolidine-1-carboxylic acid tert-butyl ester [CAS Reg. No. 141850-54-6] is prepared according to T. Nakamura et al., *J. Org. Chem.* 1992, 57, 3783–3789. Reaction of that compound with tert-butyldimethylsilyl chloride yields (2R/4R)-4-(tert-butyl-dimethyl-silanyloxy)-2-(tolyl-4-sulfonyloxymethyl)-pyrrolidine-1-carboxylic acid tert-butyl ester.

EXAMPLE 50

(3R/5R)-5-(4Amino-5-phenyl-pyrrolo[2,3-d]pyrimidin-7-ylmethyl)-pyrrolidin-3-ol

Prepared analogously to Example 17 from (2R/4R)-2-(4-amino-5-phenyl-pyrrolo[2,3-d]pyrimidin-7-ylmethyl)-4-hydroxy-pyrrolidine-1-carboxylic acid tert-butyl ester (Example 49). $^1$H-NMR (DMSO-d$_6$, ppm): 8.60 (s, 1H), 7.75 (s, 1H), 7.55–7.36 (m, 5H), 4.70 (m, 2H), 4.41 (m, 1H), 4.10 (m,1H), 3.23 (m, 2H), 2.80 (m, 1H), 1.80 (m, 1H).

Examples 51 to 54 are prepared analogously to Example 16 starting from 5-phenyl-7H-pyrrolo[2,3-d]pyrimidin-4-yl-amine (Example 1) and 4-(tolyl-4-sulfonyloxy)-piperidine- 1,2-dicarboxylic acid 1-tert-butyl ester 2-ethyl ester, 4-(tolyl4sulfonyloxy)-piperidine-1-carboxylic acid tert-butyl ester or 3-(tolyl-4-sulfonyloxy)-piperidine-1 carboxylic acid tert-butyl ester.

EXAMPLE 51
3-(4-Amino-5-phenyl-pyrrolo[2,3-d]pyrimidin-7-yl)-piperidine-1,2-dicarboxylic acid 1-tert-butyl ester 2-ethyl ester $^1$H-NMR (CD$_3$OD, ppm): 8.20 (s, 1H), 7.58 (s, 1H), 7.56–7.24 (m, 5H), 5.5 (m, 1H), 5.05 (m, 1H), 4.10 (m, 1H), 3.98 (m, 1H), 3.90 (m, 1H), 3.30 (m, 1H), 2.40 (m, 1H), 2.20 (m, 1H), 2.05 (m, 1H), 1.80 (m, 1H), 1.45 (d, 9H), 0.95 (m, 3H).

EXAMPLE 52
4-(4-Amino-5-phenyl-pyrrolo[2,3-d]pyrimidin-7-yl)-piperidine-1,2-dicarboxylic acid 1-tert-butyl ester 2-ethyl ester $^1$H-NMR (CD$_3$OD, ppm): 8.17 (s, 1H), 7.62 (s, 1H), 7.58–7.40 (m, 5H), 5.08 (m, 1H), 4.95 (m, 1H), 4.35–4.20 (m, 3H), 3.20 (m, 1H), 2.60 (m, 1H), 2.40 (m, 1H), 2.20 (m, 1H), 2.08 (m, 1H), 1.45 (d, 9H), 1.30 (m, 3H).

EXAMPLE 53
4-(4-Amino-5-phenyl-pyrrolo[2,3-d]pyrimidin-7-yl)-piperidine-1-carboxylic acid tert-butyl ester $^1$H-NMR (CDCl$_3$, ppm): 8.31 (s, 1H), 7.50–7.30 (m, 5H), 7.01 (s, 1H), 5.15 (s, 2H), 4.90 (m, 1H), 4.35 (m, 2H), 3.0 (m, 2H), 2.10 (m, 2H), 1.90 (m, 2H), 1.50 (s, 9H).

EXAMPLE 54
3-(4-Amino-5-phenyl-pyrrolo[2,3-d]pyrimidin-7-yl)-piperidine-1-carboxylic acid tert-butyl ester $^1$H-NMR (CDCl$_3$, ppm):8.31 (s, 1H), 7.52–7.32 (m, 5H), 7.02 (s, 1H), 5.20 (s, 2H), 4.80 (m, 1H), 4.30 (m, 1H), 4.00 (m, $_1$H), 3.30 (m, 1H), 3.00 (m, 1H), 2.23 (m, $_1$H), 2.05 (m, 1H), 1.49 (s, 9H).

EXAMPLE 55
3-(4-Amino-5-phenyl-pyrrolo[2,3-d]pyrimidin-7-yl)-piperidinyl-2-carboxylic acid ethyl ester dihydrochloride Prepared analogously to Example 17 starting from 3-(4-amino-5-phenyl-pyrrolo[2,3-d]pyrimidin-7-yl)-piperidine-1,2-dicarboxylic acid 1-tert-butyl ester 2-ethyl ester (Example 51). $^1$H-NMR (CD$_3$OD, ppm): 8.18 (s, 1H), 7.62 (s, 1H), 7.52–7.40 (m, 5H), 5.00 (m, 1H), 4.78 (m, 1H), 4.50–4.37 (m, 2H), 3.60 (m, 2H), 3.60 (m, 2H), 2.78 (m, 2H), 2.48 (m, 1H), 2.28 (m, 1H), 1.20 (t, 3H).

EXAMPLE 56
4-(4-Amino-5-phenyl-pyrrolo[2,3-d]pyrimidin-7-yl)-piperidine-2-carboxylic acid ethyl ester dihydrochloride Prepared analogously to Example 17 starting from 4-(4-amino-5-phenyl-pyrrolo[2,3d-pyrimidin-7-yl)-piperidine-1, 2-dicarboxylic acid 1-tert-butyl ester 2-ethyl ester (Example 52). $^1$H-NMR (CD$_3$OD, ppm): 8.41 (s, 1H), 7.60 (s, 1H), 7.52–7.42 (m, 5H), 5.50 (m, 1H), 5.00 (d, 1H), 4.18–4.02 (m, 2H), 3.80 (m, 1H), 3.38 (m,1H), 2.28 (m, 2H), 2.12 (m, 1H), 2.00 (m, 1H), 0.98 (t, 3H).

EXAMPLE 57
(5-Phenyl-7-piperidin-4-yl-7H-pyrrolo[2,3-d]pyrimidin)-4-yl-amine dihydro-chloride Prepared analogously to Example 17 starting from 4-(4-amino-5-phenyl-pyrrolo[2,3-d]-pyrimidin-7-yl)-piperidine-1-carboxylic acid tert-butyl ester (Example 53). $^1$H-NMR (DMSO-d$_6$, ppm): 8.51 (s, 1H), 7.68 (s, 1H), 7.51–7.40 (m, 5H), 5.00 (m,$_1$ 1 H), 3.48 (m, 2H), 3.18 (m, 2H), 2.40 (m, 2H), 2.18 (m, 2H).

EXAMPLE 58
(5-Phenyl-7-piperidin-3-yl-7H-pyrrolo[2,3-d]pyrimidin)-4-yl-amine dihydrochloride Prepared analogously to Example 17 starting from 3-(4-amino-5-phenyl-pyrrolo[2,3-d]-pyrimidin-7-yl)-piperidine-1-carboxylic acid tert-butyl ester (Example 54). $^1$H-NMR (DMSO-d$_6$, ppm): 8.55 (s,1H), 7.90 (s, 1H), 7.50–7.40 (m, 5H), 5.20 (m, 1H), 3.51–3.30 (m, 3H), 2.88 (m, 1H), 2.30–1.89 (m, 4H).

Examples 59–62 are prepared analogously to Example 16 starting from 5-(3-methoxyphenyl)-7H-pyrrolo[2,3-d]pyrimidin-4-yl-amine or 5-(4-methoxy-phenyl)-7H-pyrrolo[2,3-d]pyrimidin-4-yl-amine.

EXAMPLE 59
4-[4-Amino-5-(4-methoxy-phenyl)-pyrrolo[2,3-d]pyrimidin-7-yl-1-pyrrolidine-1,2-dicarboxylic acid 1-tert-butyl ester 2-ethyl ester

EXAMPLE 60
4-[4-Amino-5-(3-methoxy-phenyl)-pyrrolo[2,3-d]pyrimidin-7-yl-pyrrolidine-1,2-dicarboxylic acid 1-tert-butyl ester 2-ethyl ester

EXAMPLE 61
3-[4-Amino-5-(4-methoxy-phenyl)-pyrrolo[2,3-d]pyrimidin-7-yl-pyrrolidine-1-carboxylic acid tert-butyl ester $^1$H-NMR (CDCl$_3$, ppm): 8.32 (s, 1H), 7.40 (m, 1H), 7.10–6.86 (m, 3H), 5.50 (m, 1H), 5.30 (s, 2H), 4.01–3.82 (m, 2H), 3.69–3.48 (m, 2H), 2.45 (m,1H), 2.30 (m, 1H), 1.50 (s, 9H).

EXAMPLE 62
3-[4-Amino-5-(3-methoxy-phenyl)-pyrrolo[2,3-d]pyrimidin-7-yl1-pyrrolidine-1-carboxylic acid tert-butyl ester $^1$H-NMR (CDCl$_3$, ppm): 8.31 (s,1H), 7.38 (d, 2H), 6.99 (d, 2H), 6.90 (s,1H), 5.47 (m,1H), 5.24 (s, 2H), 3.95–3.81 (m, 2H), 3.72–3.51 (m, 2H), 2.42 (m, 1H), 2.27 (m, 1H), 1.48 (s, 9H).

Examples 63 and 64 are prepared analogously to Example 20/21 starting from 5-(4-benzyloxy-phenyl)-7H-pyrrolo[2,3-d]pyrimidin-4-yl-amine or 5-(3-benzyloxy-phenyl)-7H-pyrrolo[2,3-d]pyrimidin-4-yl-amine and 3-(toluene-4-sulfonylmethyl)-pyrrolidine-carboxylic acid tert-butyl ester.

EXAMPLE 63
5-(4-Benzyloxy-phenyl)-7-pyrrolidin-3-yl-7H-pyrrolo[2,3-d]pyrimidin-4-ylamine dihydrochloride $^1$H-NMR (DMSO-d$_6$, ppm): 8.52 (s, 1H), 7.92 (s, 1H), 7.52–7.32 (m, 7H), 7.18 (d, 2H), 5.10 (m,1H), 5.18 (s, 2H), 3.76 (m, 1H), 3.57 (m, 2H), 3.38 (m, $_1$H), 2.58 (m, $_1$H), 2.34 (m, 1H).

EXAMPLE 64
5-(3-Benzyloxy-phenyl)-7-pyrrolidin-3-yl-7H-pyrrolo[2,3-d]pyrimidin-4-ylamine dihydrochloride $^1$H-NMR (DMSO-d$_6$, ppm): 8.52 (s, 1H), 8.05 (s,1H), 7.50–7.28 (m, 6H), 7.18–7.02 (m, 3H), 5.55 (m,1H), 5.15 (s, 2H), 3.80 (m, 1H), 3.61 (m, 2H), 3.38 (m, 1H), 2.56 (m, 1H), 2.37 (m, 1H).

Example 65 is prepared analogously to Example 20/20a starting from 5-(4-benzyloxy-phenyl)-7H-pyrrolo[2,3-d]pyrimidin-4-yl-amine and 3-(toluene4-sulfonylmethyl)-pyrrolidine-1-carboxylic acid tert-butyl ester.

EXAMPLE 65
3-[4-Amino-5-(4-hydroxy-phenyl)-pyrrolo[2,3-d]pyrimidin-7-yl-pyrrolidine-1-carboxylic acid tert-butyl ester $^1$H-NMR (DMSO-d$_6$, ppm): 9.52 (s,$_1$H), 8.27 (s,1H), 7.28 (d, 2H), 6.89 (d, 2H), 6.09 (s; broad), 2H), 5.28 (m, 1H), 3.80 (m, 1H), 3.62–3.40 (m, 3H), 2.38 (m, 2H), 1.42 (s, 9H).

Example 66 is prepared analogously to Example 21 starting from 3-[4-amino-5-(4-hydroxy-phenyl)-pyrrolo[2,3-d]pyrimidin-7-yl]-pyrrolidine-1-carboxylic acid tert-butyl ester (Example 65).

EXAMPLE 66
4-(4-Amino-7-pyrrolidin-3-yl-7H-pyrrolo[2,3-d]pyrimidin-5-yl)-phenol-di-hydrochloride $^1$H-NMR (DMSO-d$_6$, ppm): 9.99 (s; broad), 1H), 9.76 (s; broad), 1H), 8.50 (s, 1H), 7.90 (s, 1H), 7.30 (d, 2H), 6.90 (d, 2H), 5.58 (m, 1H), 3.72 (m,1H), 3.49 (m, 3H), 3.31 (m, 1H), 2.52 (m, 1H), 2.30 (m, 1H).

Examples 67–70 are prepared analogously to Example 24 starting from 4-[4-amino-5-(4-methoxy-phenyl)-pyrrolo[2,3-d]pyrimidin-7-yl]-pyrrolidine-1,2-dicarboxylic acid 1-tert-butyl ester 2-ethyl ester (Example 59).

EXAMPLE 67
4-[4-Amino-5-(4-methoxy-phenyl)-pyrrolo[2,3-d]pyrimidin-7-yl]-1-(3,3-dimethyl-butyryl)-pyrrolidine-2-carboxylic acid ethyl ester

EXAMPLE 68
4-[4-Amino5-(3-methoxy-phenyl)-pyrrolo[2,3-d]pyrimidin-7-yl-1-(3,3-dimethyl-butyryl)-pyrrolidine-2-carboxylic acid ethyl ester

EXAMPLE 69
4-[4-Amino-5-(4-methoxy-phenyl)-pyrrolo[2,3-d]pyrimidin-7-yl-1-(2-amino-3-methyl-pentanoyl)-pyrrolidine-2-carboxylic acid ethyl ester

EXAMPLE 70
4-[4-Amino-5-(3-methoxy-phenyl)-pyrrolo[2,3-d]pyrimidin-7-yl]-1-(2-amino-3-methyl-pentanoyl)-pyrrolidine-2-carboxylic acid ethyl ester Examples 71–72 are prepared analogously to Example 30 starting from 4-[4-amino-5-(4-methoxy-phenyl)-pyrrolo[2,3-d]pyrimidin-7-yl]-pyrrolidine-1,2-dicarboxylic acid 1-tert-butyl ester 2-ethyl ester (Example 59 and Example 60, respectively).

EXAMPLE 71
1-{4-[4-Amino-5-(4-methoxy-phenyl)-pyrrolo[2,3-d]pyrimidin-7-yl-2-hydroxy-methyl-pyrrolidin-1-yl}-3,3-dimethyl-butan-1-one

EXAMPLE 72
1-{4-[4-Amino-5-(4-methoxy-phenyl)-pyrrolo[2,3-d]pyrimidin-7-yl]-2-hydroxy-methyl-pyrrolidin-1-yl}-3,3-dimethyl-butan-1-one Examples 73–76 are prepared analogously to Example 17.

EXAMPLE 73
4-[4-Amino-5-(4-methoxy-phenyl)-pyrrolo[2,3-d]pyrimidin-7-yl]-pyrrolidine-2-carboxylic acid ethyl ester Prepared analogously to Example 17 starting from 4-[4-amino-5-(4methoxy-phenyl)-pyrrolo[2,3-d]pyrimidin-7-yl]-pyrrolidine-1,2-dicarboxylic acid 1-tert-butyl ester 2-ethyl ester (Example 59).

EXAMPLE 74
4-[4-Amino-5-(3-methyl-phenyl)-pyrrolo[2,3-d]pyrimidin-7-yl]-pyrrolidine-2-carboxylic acid ethyl ester Prepared analogously to Example 17 starting from 4-[4-amino-5-(3-methoxy-phenyl)-pyrrolo[2,3-d]pyrimidin-7-yl]-pyrrolidine-1,2-dicarboxylic acid 1-tert-butyl ester 2-ethyl ester (Example 60).

EXAMPLE 75
5-(4-Methoxy-phenyl)-7-pyrrolidin-3-yl-7H-pyrrolo[2,3-d]pyrimidin-4-yl-amine di-hydrochloride Prepared analogously to Example 17 starting from 3-[4-amino-5-(4-methoxy-phenyl)-pyrrolo[2,3-d]pyrimidin-7-yl]-pyrrolidine-1-carboxylic acid tert-butyl ester (Example 61). $^1$H-NMR (DMSO-d$_6$, ppm): 10.0 (s; broad), 1H), 9.80 (s (broad), 1H), 8.52 (s, 1H), 7.98 (s, 1H), 7.42 (d, 2H), 7.08 (d, 2H), 5.10 (m, 1H), 3.75 (m, 1H), 3.60 (m, 2H), 3.40 (m, 1H), 2.55 (m, 1H), 2.32 (m, 1H).

EXAMPLE 76
5-(3-Methoxy-phenyl)-7-pyrrolidin-3-yl-7H-pyrrolo[2,3-d]pyrimidin-4-yl-amine di-hydrochloride Prepared analogously to Example 17 starting from 3-[4-amino-5-(3-methoxy-phenyl)-pyrrolo[2,3-d]pyrimidin-7-yl]-pyrrolidine-1-carboxylic acid tert-butyl ester (Example 62). $^1$H-NMR (DMSO-d$_6$, ppm): 10.10 (s , 1H), 9.80 (s, 1H), 8.52 (s, 1H), 8.10 (s, 1H), 7.42 (m, 1H), 7.10 (m, 2H), 6.99 (m, 1H), 5.10 (m, 1H), 3.75 (m, 1H), 3.54 (m, 2H), 3.38 (m, 1H), 2.52 (m, 1H), 2.32 (m, 1H).

Examples 77 and 78 are prepared analogously to Example 23 starting from 5-(4-benzyloxy-phenyl)-7H-pyrrolo[2,3-d]pyrimidin-4yl-amine or 5-(3-benzyloxy-phenyl) -7H-pyrrolo[2,3-d]pyrimidin-4-yl-amine and 3-(tolyl-4-sulfonyloxy)-pyrrolidine-1-carboxylic acid tert-butyl ester.

EXAMPLE 77
4-(4-Amino-7-pyrrolidin-3-yl-7H-pyrrolo[2,3-d]pyrimidin-5-yl)-phenol

EXAMPLE 78
3-(4-Amino-7-pyrrolidin-3-yl-7H-pyrrolo[2,3-d]pyrimidin-5-yl)-phenol Examples 79–3 are prepared analogously to Example 45 starting from 5-phenyl-7H-pyrrolo[2,3-d]pyrimidin-4-yl-amine and the corresponding 1-substituted 3-(tolyl4-sulfonyloxy)-pyrrolidines:

EXAMPLE 79
2-{2-[3-(4-Amino-5-phenyl-pyrrolo[2,3-d]pyrimidin-7-yl)-pyrrolidin-1-yl-ethyl-amino}ethanol

EXAMPLE 80
7-[1-(2-Morpholin-4-yl-ethyl)-pyrrolidin-3-yl]-5-phenyl-7H-pyrrolo[2,3-d]pyrimidin-4-yl-amine

EXAMPLE 81
7-[1-(2-Imidazol-1-yl-ethyl)-pyrrolidin-3-yl]-5-phenyl-7H-pyrrolo[2,3-d]pyrimidin-4-yl-amine

EXAMPLE 82
2-[3-(4-Amino-5-phenyl-pyrrolo[2,3-d]pyrimidin-7-yl)-pyrrolidin-1-yl]-ethanol

EXAMPLE 83
7-[1-(2-Methoxy-ethyl)-pyrrolidin-3-yl]-5-phenyl-7-pyrrolo[2,3-d]pyrimidin-4-yl-amine Examples 84–99 are prepared analogously to Example 20 starting from 5-(4-benzyloxy-phenyl-7H-pyrrolo[2,3-d]pyrimidin-4-yl-amine or 5-(3-benzyloxy-phenyl-7H-pyrrolo[2,3-d]pyrimidin-4-yl-amine and the corresponding 1-substituted 3-(tolyl-4-sulfonyloxy)-pyrrolidines:

EXAMPLE 84
4-(4-Amino-7-{1-[2-(2-hydroxy-ethylamino)-ethyl]-pyrrolidin-3-yl}-7H-pyrrolo-[2,3-d]pyrimidin-5-yl)-phenol

EXAMPLE 85
3-(4Amino-7-{1-[2-(2-hydroxy-ethylamino)-ethyl]-pyrrolidin-3-yl}-7H-pyrrolo-[2,3-d]pyrimidin-5-yl)-phenol

EXAMPLE 86
4-{4-Amino-7-[1-(2-morpholin-4-yl-ethyl)-pyrrolidin-3-yl]-7H-pyrrolo[2,3-d]pyrimidin-5-yl}-phenol

EXAMPLE 87
3-{4-Amino-7-[1-(2-morpholin-4-yl-ethyl)-pyrrolidin-3-yl]-7H-Pyrrolo[2,3-d]pyrmidin-5-yl}-phenol

EXAMPLE 88
4-{4-Amino-7-[1-(2-imidazol-1-yl-ethyl)-pyrrolidin-3-yl]-7H-pyrrolo[2,3-d]pyrimidin-5-yl}-phenol

EXAMPLE 89
3-{4-Amino-7-[1-(2-imidazol-1-yl-ethyl)-pyrrolidin-3-yl]-7H-pyrrolo[2,3-d]pyrimidin-5-yl}-phenol

EXAMPLE 90
4-{4-Amino-7-[1-(2-methoxy-ethyl)-pyrrolidin-3-yl]-7H-pyrrolo[2,3-d]pyrimidin-5-yl}-phenol

EXAMPLE 91
3-{4-Amino-7-[1-(2-methoxy-ethyl)-pyrrolidin-3-yl]-7H-pyrrolo[2,3-d]pyrimidin-5-yl}-phenol

EXAMPLE 92
4-{4-Amino-7-[1-(2-imidazo-1-yl-ethyl)-pyrrolidin-3-yl]-7H-pyrrolo[2,3-d]pyrimidin-5-yl}-phenol

EXAMPLE 93
3-{4-Amino-7-[1-(2-imidazol-1-yl-ethyl)-pyrrolidin-3-yl]-7H-pyrrolo2,3-d]pyrimidin-5-yl}-phenol

EXAMPLE 94
4-{4-Amino-7-[1-(2-hydroxy-ethyl)-pyrrolidin-3-yl]-7H-pyrrolo[2,3-d]pyrimidin-5-yl}-phenol

EXAMPLE 95
3-{4-Amino-7-[1-(2-hydroxy-ethyl)-pyrrolidin-3-yl]-7H-pyrrolo[2,3-d]pyrimidin-5-yl}-phenol

EXAMPLE 96
{3-[4-Amino-5-(3-benzyloxy-phenyl)-pyrrolo[2,3-d]pyrimidin-7-yl]-pyrrolidin-1-yl}-acetic acid methyl ester $^1$H-NMR (CDCl$_3$, ppm): 8.3 (s, 1H), 7.49–7.39 (M, 7H), 7.1 (m,$_1$ 2H), 6.95 (m. H), 5.5 (m, 1H), 5.12 (s, 2H), 5.05 (s, 2H), 3.71 (s, 1H), 3.42 (q, 2H), 3.29–3.13 (m, 2H), 2.99 (m, H), 2.70–2.51 (m, 2H), 2.08 (m, 1H).

EXAMPLE 97
{3-[4-Amino-5-(3-hydroxy-phenyl)-pyrrolo[2,3-d]pyrimidin-7-yl]-pyrrolidin-1-yl}acetic acid methyl ester $^1$H-NMR (DMSO-d$_6$, ppm): 9.59 (s, 1H), 8.12 (s,1H), 7.28 (t, 1H), 6.82 (m, 2H), 6.72 (d, 1H), 6.10 (s; broad), 2H)$_1$ 5.11 (m , H) 3.62 (s, 3H)6 3.45 (q, 2H), 3.16 2.82 (m, 3H), 2.60 (m, 3H), 2.42 (m, 1H) 1.95 (m, 1H).

EXAMPLE 98
2-{3-[4-Amino-5-(3-hydroxy-phenyl)-pyrrolo[2,3-d]pyrimidin-7-yl]-pyrrolidin-1-yl}N,N-dimethyl-acetamide $^1$H-NMR (CD$_3$OD, ppm): 8.12 (s, 1H), 7.53 (s, 7H), 7.29 (m, 1H), 6.96 (m, 2H), 6.80 (m, 1H), 5.41 (m s, 2H), 3.50 (m, 2H), 3.30 (m, 3H), 3.20 (m, 1H), 3.10 (s, 3H), 2.93 (s, 3H), 2.88 (m, 1H), 2.59 (m, 2H), 2.09 (m, 1H).

EXAMPLE 99
2-{3-[4-Amino-5-(3hydroxy-phenyl)-pyrrolo[2,3-d]pyrimidin-7-yl]-pyrrolidin-1-yl}acetamide $^1$H-NMR (DMSO-d$_6$, ppm): 9.70 (s, 1H), 8.12 (s, 1H), 7.58 (s, 1H), 7.46 (s; broad), 1H) ) 7.25 (t, 1H), 7.1 5 (s; broad), 11 ), 6.88 (m, 2H), 6.79 (m, 1 (), 6.12 (s; broad), 2H), 5.38 (m, 1H), 3.40 (m, 1H), 2.93 (m, 2H), 2.57 (m, 1H), 2.42 (m, 1H), 2.05 (m, 1H).

Examples 100–109 are prepared analogously to Example 45 starting from 5-(4-methoxy-phenyl)-7H-pyrrolo[2,3-d]pyrimidin-4-yl-amine or 5-(3-methoxyphenyl)-7H-pyrrolo[2,3-d]pyrimidin-4-yl-amine and the corresponding 1-substituted 3-(tolyl-4-sulfonyloxy)-pyrrolidines.

EXAMPLE 100
2-(2-{3-[4-Amino-5-(4-methoxy-phenyl)-pyrrolo[2,3-d]pyrrolidin-7-yl]-pyrrolidin-1-yl}-ethylamino)-ethanol

EXAMPLE 101
1-(2-{3-[4-Amino-5-(3-methoxy-phenyl)-pyrrolo[2,3-d]pyrimidin-7-yl]-pyrrolidin-1-yl}-ethylamino)-ethanol

EXAMPLE 102
5-(4-Methoxy-phenyl)-7-[1-(2-morpholin-4-yl-ethyl)-pyrrolidin-3-yl]-7H-pyrrolo-[2,3-d]pyrimidin-4-yl-amine

EXAMPLE 103
5-(3-Methoxy-phenyl)-7-[1-(2-morpholin-4-yl-ethyl)-pyrrolidin-3-yl]-7H-pyrrolo-[2,3-d]pyrimidin-4-yl-amine

EXAMPLE 104
7-[1-(2-Imidazol-1-yl-ethyl)-pyrrolidin-3-yl]-5-(4-methoxy-phenyl)-7H-pyrrolo-[2,3-d]pyrimidin-4-yl-amine

EXAMPLE 105
7-[1-(2-Imidazol-1-yl-ethyl)-pyrrolidin-3-yl]-5-(3-methoxy-phenyl)-7H-pyrrolo-[2,3-d]pyrimidin-4-yl-amine

EXAMPLE 106
7-[1-(2-Methoxy-ethyl)-pyrrolidin-3-yl]-5-(4-methoxy-phenyl)-7H-pyrrolo[2,3-d]pyrimidin-4-yl-amine

EXAMPLE 107
7-[1-(2-Methoxy-ethyl)-pyrrolidin-3-yl]-5-(3-methoxy-phenyl) -7H-pyrrolo[2,3-d]pyrimidin-4-yl-amine

EXAMPLE 108
{3-[4-Amino-5-(3-methoxy-phenyl)-pyrrolo[2,3-d]pyrimidin-7-yl]-pyrrolidin-1-yl}acetic acid methyl ester Examples 109 and I1I0 are prepared analogously to Example 16 starting from 5-(4-methoxy-phenyl) -7H-pyrrolo[2,3-d]pyrimidin-4-yl-amine or 5-(3-methoxy-phenyl)-7H-pyrrolo-[2,3-d]pyrimidin-4-yl-amine and 4-(toyl-4-sulfonyloxy)-piperidine-1,2-dicarboxylic acid 1-tert-butyl ester 2-ethyl ester.

EXAMPLE 109
4-[4-Amino-5-(4-methoxy-phenyl)-pyrrolo[2,3-d]pyrimidin-7-yl-1-piperidine-1,2-dicarboxylic acid 1-tert-butyl ester 2-ethyl ester

EXAMPLE 110
4-[4-Amino-5-(3-methoxy-phenyl)-pyrrolo[2,3-d]pyrimidin-7-yl]-piperidine-1,2-dicarboxylic acid 1-tert-butyl ester 2-ethyl ester Examples 111–115 are prepared analogously to Example 20 starting from 5-(4-benzyloxy-phenyl)-7H-pyrrolo[2,3-d]

pyrimidin-4-yl-amine or 5-(3-benzyloxy-phenyl) -7H-pyrrolo[2,3-d]pyrimidin-4-yl-amine and 4-(tolyl-4-sulfonyloxy)-piperidine-1,2-dicarboxylic acid 1-tert-butyl ester 2-ethyl ester.

EXAMPLE 111
4-[4-Amino-5-(3-benzyloxy-phenyl)-pyrrolo[2,3-d]pyrimidin-7-yl]-piperidine-1-carboxylic acid tert-butyl ester $^1$H-NMR (CDCl$_3$, ppm): 8.30 (s, 1H), 7.40 (m, 6H), 7.10–6.92 (m, 4H), 5.12 (s, 4H), 4.88 (m, 1H), 4.32 (m, 2H), 2.96 (m, 2H), 2.11 (m, 1H), 1.97–1.82 (m, 3H), 1.49 (s, 9H).

EXAMPLE 112
4-[4-Amino-5-(4-hydroxy-phenyl)-pyrrolo[2,3-d]pyrimidin-7-yl]-piperidine-1,2-dicarboxylic acid 1-tert-butyl ester 2-ethyl ester

EXAMPLE 113
4-[4-Amino-5-(3-hydroxy-phenyl)-pyrrolo 2,3-d]pyrimidin-7-yl]-piperidine-1,2-dicarboxylic acid 1-tert-butyl ester 2-ethyl ester Examples 114–117 are prepared analogously to Example 17.

EXAMPLE 114
4-[4-Amino-5-(4-methoxy-phenyl)-pyrrolo[2,3-d]pyrimidin-7-yl]-piperidine-2-carboxylic acid ethyl ester Prepared analogously to Example 17 starting from 4-[4-amino5-(4-methoxy-phenyl)-pyrrolo[2,3-d]pyrimidin-7-yl]-piperidine-1,2-dicarboxylic acid 1-tert-butyl ester 2-ethyl ester (Example 100).

EXAMPLE 115
4-[4-Amino5-(3-methoxy-pheny)-pyrrolo[2,3-d]pyrimidin-7-yl]-piperidine-2-carboxylic acid ethyl ester Prepared analogously to Example 17 starting from 4-[4-amino-5-(3-methoxy-phenyl)-pyrrolo[2,3-d]pyrimidin-7-yl]-piperidine-1,2-dicarboxylic acid 1-tert-butyl ester 2-ethyl ester (Example 110).

EXAMPLE 116
4-[4-Amino-5-(4-hydroxy-phenyl)-pyrrolo[2,3-d]pyrimidin-7-yl]-piperidine-2-carboxylic acid ethyl ester Prepared analogously to Example 17 starting from 4-[4-amino-5-(4-hydroxy-phenyl)-pyrrolo-[2,3-d]pyrimidin-7-yl]-piperidine-1,2-dicarboxylic acid 1-tert-butyl ester 2-ethyl ester (Example 112).

EXAMPLE 117
4-[4-Amino-5-(3-hydroxy-phenyl)-pyrrolo[2,3-d]pyrimidin-7-yl]-piperidine-2-carboxylic acid ethyl ester Prepared analogously to Example 17 starting from 4-[4-amino-5-(3-hydroxy-phenyl)-pyrrolo-[2,3-d]pyrimidin-7-yl]-piperidine-1,2-dicarboxylic acid 1-tert-butyl ester 2-ethyl ester (Example 113).

Examples 118 and 119 are prepared analogously to Example 16 starting from 5-(4-methoxy-phenyl)-7H-pyrrolo[2,3-d]pyrimidin-4-yl-amine or 5-(3-methoxy-phenyl)-7H-pyrrolo-[2,3-d]pyrimidin-4-yl-amine and 4-(tolyl-4-sulfonyloxy)-piperidine-1-carboxylic acid tert-butyl ester.

EXAMPLE 118
4-[4-Amino-5-(4-methoxy-phenyl)-pyrrolo[2,3-d]pyrimidin-7-yl]-piperidine-1-carboxylic acid tert-butyl ester

EXAMPLE 119
4-[4-Amino-5-(3-methoxy-phenyl)-pyrrolo[2,3-d]pyrimidin-7-yl]-piperidine-1-carboxylic acid tert-butyl ester $^1$H-NMR (CDCl$_3$, ppm): 8.32 (s, 1H), 8.05 (s, 1H), 7.38 (t, 1H), 7.08–6.87 (m, 3H), 5.22 (s, 2H), 4.90 (m, 1H), 4.31 (m, 2H), 3.88 (s, 3H), 2.97 (m, 2H), 2.10 (m, 2H), 1.90 (m, 2H), 1.50 (s, 9H).

Example 120 is prepared analogously to Example 16 starting from 5-(3-fluoro-phenyl)-7H-pyrrolo[2,3-d]pyrimidin-4-yl-amine and 4-(tolyl-4-sulfonyloxy)-piperidine-1-carboxylic acid tert-butyl ester.

EXAMPLE 120
4-[4-Amino-5-(3-fluoro-phenyl)-pyrrolo[2,3-d]pyrimidin-7-yl]-piperidine-1-carboxylic acid tert-butyl ester $^1$H-NMR (CDCl$_3$, ppm): 8.38 (s, 1H), 7.52–7.38 (m, 1H), 7.28–7.02 (m, 3H), 7.00 (s, 1H), 4.90 (m, 1H), 4.32 (m, 2H), 2.98 (m, 2H), 2.10 (m, 2H), 1.91 (m, 1H), 1.50 (s, 9H).

Examples 121 and 122 are prepared analogously to Example 20 starting from 5-(4-benzyloxy-phenyl) -7H-pyrrolo[2,3-d]pyrimidin-4-yl-amine or 5-(3-benzyloxy-phenyl) -7H-pyrrolo[2,3-d]pyrimidin-4-yl-amine and 4-(tolyl-4-sulfonyloxy)-piperidine-1-dicarboxylic acid tert-butyl ester.

EXAMPLE 121
4-[4-Amino-5-(4-hydroxy-phenyl)-pyrrolo[2,3-d]pyrimidin-7-yl]-piperidine-1-carboxylic acid tert-butyl ester

EXAMPLE 122
4-[4-Amino-5-(3-hydroxy-phenyl)-pyrrolo[2,3-d]pyrimidin-7-yl]-piperidine-1-carboxylic acid tert-butyl ester $^1$H-NMR (DMSO-d$_6$, ppm): 9.58 (s, 1H), 8.13 (s, 1H), 7.49 (s,1H), 7.28 (t,1H), 6.88 (m, 2H), 6.78 (m, 1H), 6.28 (s; broad), 2H), 4.78 (m, 1H), 4.12 (m, 2H), 2.96 (m, 2H), 1.90 (m, 4H), 1.42 (s, 9H).

Examples 123–126 are prepared analogously to Example 17.

EXAMPLE 123
5-(4-Methoxy-phenyl)-7-piperidin-4-yl-7H-pyrrolo[2,3-d]pyrimidin-4-yl-amine Prepared analogously to Example 17 starting from 4-[4-amino-5-(4-methoxy-phenyl)-pyrrolo[2,3-d]pyrimidin-7-yl]-piperidine-1-carboxylic acid tert-butyl ester (Example 118).

EXAMPLE 124
5-(3-Methoxy-phenyl)-7-piperidin-4-yl-7H-pyrrolo[2,3-d]pyrimidin-4-yl-amine Prepared analogously to Example 17 starting from 4-[4-amino-5-(3-methoxy-phenyl)-pyrrolo[2,3-d]pyrimidin-7-yl]-piperidine-1-carboxylic acid tert-butyl ester (Example 119). $^1$H-NMR (DMSO-d$_6$, ppm): 9.48 (m; broad), 1H), 9.30 (m; broad), 1H), 8.52 (s, 1H), 7.70 (s, 1H), 7.42 (t, 1H), 7.12 (m, 2H), 6.99 (m, 1H), 5.00 (m, 1H), 3.82 (s, 3H), 3.46 (m, 2H), 3.12 (m, 2H), 2.40 (m, 2H), 2.12 (m, 2H).

EXAMPLE 125
4-(4-Amino-7-piperidin-4-yl-7H-pyrrolo[2,3-d]pyrimidin-5-yl)-phenol Prepared analogously to Example 17 starting from 4-[4-amino-5-(4-hydroxy-phenyl)-pyrrolo-[2,3-d]pyrimidin-7-yl]-piperidine-1-carboxylic acid tert-butyl ester (Example 121).

EXAMPLE 126
3-(4-Amino-7-piperidin-4-yl-7H-pyrrolo[2,3-d]pyrimidin-5-yl)-phenol Prepared analogously to Example 17 starting from 4-[4-amino-5-(3-hydroxy-phenyl)-pyrrolo [2,3-d]pyrimidin-7-

EXAMPLE 127
5-(3-Fluoro-thenyl)-7-piperidin-4-yl-7H-pyrrolo[2,3-d]pyrimidin-4-ylamine di-hydrochloride Prepared analogously to Example 17 starting from 4-[4-amino-5-(3-fluoro-phenyl)-pyrrolo-[2,3-d]pyrimidin-7-yl]-piperidine-1-carboxylic acid tert-butyl ester (Example 120). $^1$H-NMR (DMSO-$d_6$, ppm): 9.45 (m, 1H), 9.32 (m, 1H), 8.58 (s, 1H), 7.78 (s, 1H), 7.55 (m, 1H), 7.38–7.15 (m, 3H), 5.00 (m, 1H), 3.41 (m, 2H), 3.15 (m, 2H), 2.35 (m, 2H), 2.14 (m, 2H).

Examples 128–142 are prepared analogously to Example 16 starting from 5-phenyl-7H-pyrrolo[2,3-d]pyrimidin-4-yl-amine or 5-(4-methoxy-phenyl)-7H-pyrrolo[2,3-d]pyrimidin-4yl-amine or 5-(3-methoxy-phenyl)-7H-pyrrolo[2,3-d]pyrimidin-4yl-amine and the correspondingly 1-substituted 4-(tolylsulfonyloxy)-piperidines.

EXAMPLE 128
7-[1-(2-Morpholin-4-yl-ethyl)-piperidin-4-yl]-5-phenyl-7H-pyrrolo[2,3-d]pyrimidin-4-yl-amine

EXAMPLE 129
7-{1-[2-(2-Amino-ethoxy)-ethyl]-piperidin-4-yl}-5-phenyl-7H-pyrrolo[2,3-d]pyrimidin-4-yl-amine

EXAMPLE 130
7-[1-(2-Imidazol-1-yl-ethyl)-piperidin-4-yl]-5-phenyl-7H-pyrrolo[2,3-d]pyrimidin-4-yl-amine

EXAMPLE 131
7-[1-(2-Methoxy-ethyl)-piperidin-4-yl]-5-phenyl-7H-pyrrolo[2,3-d]pyrimidin-amine

EXAMPLE 132
2-[4-(4-Amino-5-phenyl-pyrrolo[2,3-d]pyrimidin-7-yl)-piperidin-1-yl]-ethanol

EXAMPLE 133
5-(4-Methoxy-phenyl)-7-[1-(2-morpholin-4-yl-ethyl)-piperidin--4-yl]-7H-pyrrolo-[2,3-d]pyrimidin-4-yl-amine

EXAMPLE 134
5-(3-Methoxy-phenyl)-7-[1-(2-morpholin-4-yl-ethyl)-piperidin-4-ethyl)-piperidin-4-yl]-7H-pyrrolo-[2,3-d]pyrimidin-4-yl-amine

EXAMPLE 135
7-{1-[2-(2-Amino-ethoxy)-ethyl]-piperidin-4-yl}-5-(4-methoxy-phenyl)-7H-pyrrolo[2,3-d]pyrimidin-4-yl-amine

EXAMPLE 136
7-{1-[2-(2-Amino-ethoxy)-ethyl]-piperidin-4-yl}-5-(3-methoxy-phenyl)-7H-pyrrolo[2,3-d]pyrimidin-4-yl-amine

EXAMPLE 137
7-[1-(2-Imidazol-1-yl-ethyl)-piperidin-4-yl]-5-(4-methoxy-phenyl)-7H-pyrrolo-[2,3-d]pyrimidin-4-yl-amine

EXAMPLE 138
7-[1-(2-Imidazol-1-yl-ethyl)-piperidin-4-yl]-5-(3-methoxy-phenyl)-7H-pyrrolo-[2,3-d]pyrimidin-4-yl-amine

EXAMPLE 139
7-[1-(2-Methoxy-ethyl)-piperidin-4-yl]-5-(4-methoxy-phenyl)-7H-pyrrolo[2,3-d]pyrimidin-4-yl-amine

EXAMPLE 140
7-[1-(2-Methoxy-ethyl)-piperidin-4-yl]-5-(3-methoxy-phenyl)-7H-pyrrolo[2,3-d]pyrimidin-4-yl-amine

EXAMPLE 141
2-{4-[4-Amino-5-(4-methoxy-phenyl)-pyrrolo[2,3-d]pyrimidin-7-yl]-piperidin-1-yl}-ethanol

EXAMPLE 142
2-{4-[4-Amino-5-(3-methoxy-phenyl)-pyrrolo[2,3-d]pyrimidin-7-yl]-piperidin-1-yl}-ethanol

EXAMPLE 143
2-{4-[4-Amino-5-(3-methoxy-phenyl)-pyrrolo[2,3-d]pyrimidin-7-yl]-piperidin-1-yl}-ethanol
$^1$H-NMR (CDCl$_3$, ppm): 8.32 (s, 1H), 7.36 (t, 1H), 7.09–6.90 (m, 4H), 5.20 (s, 2H), 4.75 (m, 1H), 3.85 (s, 3H), 3.68 (t, 2H), 3.09 (m, 2H), 2.61 (t, 2H), 2.35 (m, 2H), 2.19–1.90 (m, 4H).

EXAMPLE 144
{4-[4-Amino-5-(3-methoxy-phenyl)-pyrrolo[2,3-d]pyrimidin-7-yl]-piperidin-1-yl}-acetic acid methyl ester
$^1$H-NMR (CDCl$_3$, ppm): 8.31 (s, 1H), 7.38 (t,$_1$H), 7.10–6.88 (m, 4H), 5.18 (s, 2H), 4.75 (m, 1H), 3.85 (s, 3H), 3.74 (s, 3H), 3.30 (s, 2H), 3.10 (m, 2H), 2.49 (m, 2H), 2.21–2.02 (m, 4H).

EXAMPLE 145
2-{4-[4-Amino-5-(3-methoxy-phenyl)-pyrrolo[2,3-d]pyrimidin-7-yl]-piperidin-1-yl}-acetamide
$^1$H-NMR (DMSO-$d_6$, ppm): 8.13 (s, 1H), 7.48 (s, 1H). 7.38 (t, 1H), 7.22 (s, 1H), 7.18 (s, 1H), 7.07–7.01 (m, 2H), 6.90 (m, $_1$H), 6.12 (s; broad, 2H), 4.61 (s, $_1$H), 3.82 (s, 3H), 3.35 (m, 2H), 2.98 (s, 2H), 2.31 (m, 2H), 2.16 (m, 2H), 1.88 (m, 2H).

EXAMPLE 146
2-{4-[4-Amino-5-(3-methoxy-phenyl)-pyrrolo[2,3-d]pyrimidin-7-yl]-piperidin-1-yl}-N,N-dimethyl!-acetamide
M.p.: 214–216° C.

EXAMPLE 147
{4-[4-Amino-5-(3-methoxy-phenyl)-pyrrolo[2,3-d]pyrimidin-7-yl]-piperidin-1-yl}-acetic acid
$^1$H-NMR (DMSO-$d_6$, ppm): 8.30 (s, 1H), 7.58 (s, 1H), 7.40 (t, 1H). 7.09–6.90 (m, 3H), 4.80 (m, 1H), 4.12 (s, 2H), 3.70 (s, 3H), 3.60 (m, 2H), 3.30 (m, 2H), 2.50 (m, 2H), 2.18 (m, 2H).

Examples 148–157 are prepared analogously to Example 20 starting from 5-(4-benzyloxy-phenyl)-7H-pyrrolo[2,3-d]pyrimidin-4-yl-amine or 5-(3-benzyloxy-phenyl)-7H-pyrrolo[2,3-d]pyrimidin-4-yl-amine and the correspondingly 1-substituted 4-(tolyl4-sulfonyloxy)-piperidines.

EXAMPLE 148
4-{4-Amino-7-[1-(2-hydroxy-ethyl)-piperidin-4-yl]-7H-pyrrolo[2,3-d]pyrimidin-5-yl}-phenol

EXAMPLE 149
3-{4-Amino-7-[1-(2-hydroxy-ethyl)-piperidin-4-yl]-7H-pyrrolo[2,3-d]pyrimidin-5-yl}-phenol

EXAMPLE 150
4-{4-Amino-7-[1-(2-morpholin-4-yl-ethyl)-piperidin-4-yl]-7H-pyrrolo[2,3-d]pyrimidin-5-yl}-phenol

EXAMPLE 151
3-{4-Amino-7-[1-(2-morpholin-4-yl-ethyl)-piperidin-4-yl]-7H-pyrrolo[2,3-d]pyrimidin-5-yl}-phenol

EXAMPLE 152
4-(4-Amino-7-{1-[2-(2-amino-ethoxy)-ethyl]-piperidin-4-yl}-7H-pyrrolo[2,3-d]pyrimidin-5-yl)-phenol

EXAMPLE 153
3(4-Amino-7-{1-[2-(2-amino-ethoxy)-ethyl]-piperidin-4-yl}-7H-pyrrolo[2,3-d]pyrimidin-5-yl)-phenol

EXAMPLE 154
4-{4-Amino-7-[1-(2-methoxy-ethyl)-piperidin-yl]-7H-pyrrolo[2,3-d]pyrimidin-5-yl}-phenol

EXAMPLE 155
3-{4-Amino-7-[1-(2-methoxy-ethyl)-piperidin-4-yl]-7H-pyrrolo[2,3-d]pyrimidin-5-yl}-phenol

EXAMPLE 156
4-{4-Amino-7-[1-(2-imidazol-1-yl-ethyl)-piperidin-4-yl] 7H-pyrrolo[2,3-d]pyrimidin-5-yl}-phenol

EXAMPLE 157
3-{4-Amino-7-[1-(2-imidazol-1-yl-ethyl)-piperidin-4-yl]-7H-pyrrolo[2,3-d]pyrimidin-5-yl}-phenol

EXAMPLE 158
{4-[4-Amino-5-(3-hydroxy-phenyl)-pyrrolo[2,3-d]-pyrimidin-7-yl]-piperidin-1-yl}-acetic acid methyl ester

EXAMPLE 159
2-{4-[4-Amino-5-(3-hydroxy-phenyl)-pyrrolo[2,3-d]pyrimidin-7-yl]-piperidin-1-yl}-N,N-dimethyl-acetamide

EXAMPLE 160
2-{4-[4-Amino-5-(3-hydroxy-phenyl)-pyrrolo[2,3-d]pyrimidin-7-yl]-piperidin-1-yl}-acetamide

EXAMPLE 161
{4-[4-Amino-5-(3-hydroxy-phenyl)-pyrrolo[2,3-d]pyrimidin-7-yl]-piperidin-1-yl}-acetic acid

EXAMPLES A–B
Pharmaceutical compositions

Example A
Tablets each comprising 50 mg of active ingredient

| Composition (10 000 tablets) | |
|---|---|
| active ingredient | 500.0 g |
| lactose | 500.0 g |
| potato starch | 352.0 g |
| gelatin | 8.0 g |
| talc | 60.0 g |
| magnesium stearate | 10.0 g |
| silica (highly dispersed) | 20.0 g |
| ethanol | q.s. |

The active ingredient is mixed with the lactose and 292 g of the potato starch and the mixture is moistened with an ethanolic solution of the gelatin and granulated through a sieve. After drying, the remaining potato starch, the magnesium stearate, the talc and the silica are mixed in and the mixture is compressed to form tablets each weighing 145 mg and comprising 50 mg of active ingredient, which may, if desired, be provided with dividing notches for finer adaptation of the dose.

Example B
Film-coated tablets, each comprising 100 mg of active ingredient:

| Composition (1000 film-coated tablets) | |
|---|---|
| active ingredient | 100.0 g |
| lactose | 100.0 g |
| corn starch | 70.0 g |
| talc | 8.5 g |
| calcium stearate | 1.5 g |
| hydroxypropylmethylcellulose | 2.36 g |
| shellac | 0.64 g |
| water | q.s. |
| dichloromethane | q.s. |

The active ingredient, the lactose and 40 g of the corn starch are mixed, and the mixture is moistened with a paste, prepared from 15 g of the corn starch and water (with heating), and granulated. The granules are dried, and the remaining corn starch, the talc and the calcium stearate are mixed with the granules. The mixture is compressed to form tablets (each weighing 280 mg), which are then coated with a solution of the hydroxypropylmethylcellulose and the shellac in dichloromethane (final weight of each film-coated tablet: 283 mg).

I claim:
1. A Compound of formula I

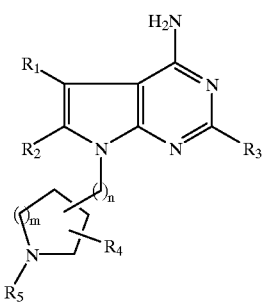

wherein $R_1$ is phenyl unsubstituted or substituted by one, two or three substituents selected from the group consisting of lower alkyl, hydroxy-lower alkyl, phenyl, lower alkoxy, phenyl-lower alkoxy, $C_1$–$C_3$alkylenedioxy, cyano, and halogen;

$R_2$ and $R_3$ are simultaneously or each independently of the other hydrogen, lower alkyl or halogen;

$R_4$ is hydrogen, hydroxy, lower alkyl, lower alkoxy, lower alkyleneoxy-lower alkyl, lower alkoxycarbonyl, N-lower alkylaminocarbonyl or N,N-di-lower alkylaminocarbonyl;

$R_5$ is hydrogen, lower alkyl, lower alkylcarbonyl or lower alkoxycarbonyl;

wherein alkyl, by itself or as a constituent of another group, may be unsubstituted or substituted lay a substituent selected from the group consisting of halogen, hydroxy, lower alkoxy, trifluoromethyl, morpholin-4-yl, amino, N-lower alkylamino, and N,N-di-lower alkylamino;

m is 1 or 2;

n is an integer from 0 to 4 inclusive;

or pharmaceutically acceptable salts thereof.

2. A compound according to claim 1 wherein $R_2$ and $R_3$ are hydrogen.

3. A compound according to claim 1 wherein $R_4$ is hydrogen, lower alkyl, lower alkoxy, lower alkyleneoxy-lower alkyl or lower alkoxycarbonyl and n is 0 or 1.

4. A compound according to claim 1 wherein n is 0.

5. A method of inhibiting the bone absorption ability of osteoclasts comprising administering to patients in need of such inhibiting a therapeutically effective amount of a compound according to claim 1.

6. Pharmaceutical compositions comprising a compound according to claim 1 and at least one pharmaceutically acceptable carrier.

7. Process for the preparation of a compound of formula I according to claim 1, which process comprises (a) subjecting a compound of formula II

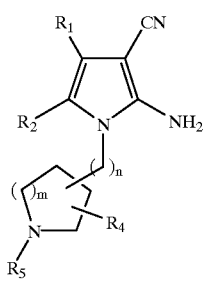

(II)

to a ring closure reaction with synthesis of the pyrimidine ring, or (b) subjecting a compound of formula III

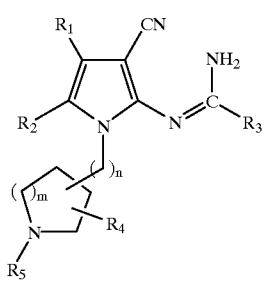

(III)

to a ring closure reaction with synthesis of the pyrimidine ring, or (c) reacting a compound of formula IV

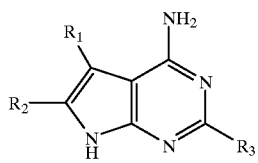

(IV)

with a compound of formula V

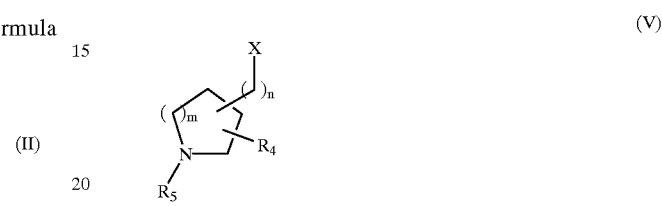

(V)

wherein X is a leaving group, or (d) reacting a compound of formula VI

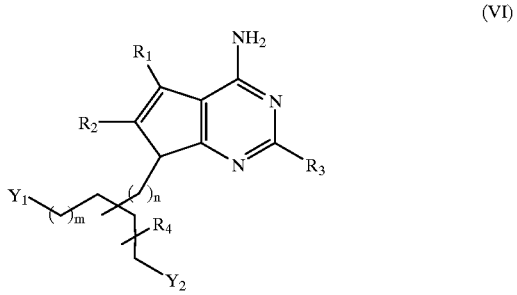

(VI)

wherein $Y_1$ and $Y_2$ are suitable leaving groups, with a compound of formula VII

$R_5$—$NH_2$     (VII)

and, if desired, converting a resulting salt into the free compound or into a different salt, and/or, if desired, converting a resulting free compound of formula I having salt-forming properties into a salt.

* * * * *

UNITED STATES PATENT AND TRADEMARK OFFICE
CERTIFICATE OF CORRECTION

PATENT NO. : 6,051,577
DATED : April 18, 2000
INVENTOR(S) : Eva Altmann

It is certified that error appears in the above-indentified patent and that said Letters Patent is hereby corrected as shown below:

Title page, left column, section [30], should read:

[30] Foreign Application Priority Data

Mar. 15, 1996 [CH] Switzerland .......... 694/96

Under column 36, line 59, "lay" should read -- by -- .

UNITED STATES PATENT AND TRADEMARK OFFICE
CERTIFICATE OF CORRECTION

PATENT NO. : 6,051,577
DATED : April 18, 2000
INVENTOR(S) : Eva Altmann

Page 2 of 2

It is certified that error appears in the above-indentified patent and that said Letters Patent is hereby corrected as shown below:

Under column 38, delete structure (VI) and replace with the following structure:

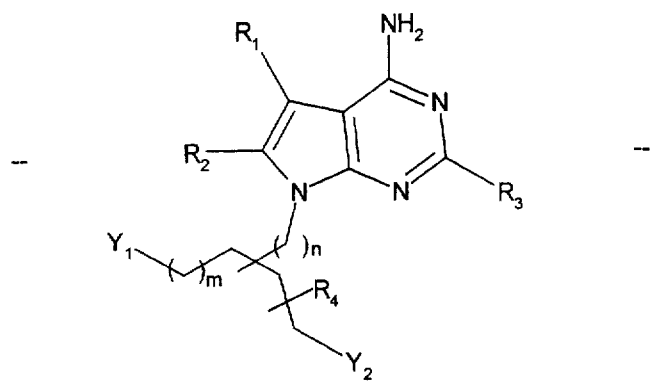

Signed and Sealed this

Third Day of April, 2001

*Attest:*

NICHOLAS P. GODICI

*Attesting Officer*  Acting Director of the United States Patent and Trademark Office